(12) United States Patent
Knopp et al.

(10) Patent No.: US 8,585,693 B2
(45) Date of Patent: *Nov. 19, 2013

(54) METHODS AND DEVICES FOR TREATING TISSUE

(75) Inventors: Peter G. Knopp, Pleasanton, CA (US); Bankim H. Mehta, San Ramon, CA (US)

(73) Assignee: Syneron Medical Ltd., Yokneam Illit (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/429,008

(22) Filed: Mar. 23, 2012

(65) Prior Publication Data

US 2013/0060246 A1    Mar. 7, 2013

Related U.S. Application Data

(63) Continuation of application No. 11/676,235, filed on Feb. 16, 2007, now Pat. No. 8,142,426.

(60) Provisional application No. 60/829,607, filed on Oct. 16, 2006.

(51) Int. Cl.
*A61B 18/14* (2006.01)
*A61B 18/18* (2006.01)

(52) U.S. Cl.
USPC .................................. 606/31; 606/32; 606/41

(58) Field of Classification Search
USPC .......................................... 606/20–26, 32–52
See application file for complete search history.

(56) References Cited

U.S. PATENT DOCUMENTS

| | | | |
|---|---|---|---|
| 4,016,886 A | 4/1977 | Doss et al. |
| 4,306,568 A | 12/1981 | Torre |
| 4,712,559 A | 12/1987 | Turner |
| 4,837,049 A | 6/1989 | Byers et al. |
| 4,860,752 A | 8/1989 | Turner |
| 4,969,468 A | 11/1990 | Byers et al. |
| 5,000,752 A | 3/1991 | Hoskin et al. |
| 5,242,455 A | 9/1993 | Skeens et al. |
| 5,279,544 A | 1/1994 | Gross et al. |
| 5,374,283 A | 12/1994 | Flick |
| 5,403,311 A | 4/1995 | Abele et al. |
| 5,449,378 A | 9/1995 | Schouenborg |
| 5,457,041 A | 10/1995 | Ginaven et al. |
| 5,458,596 A | 10/1995 | Lax et al. |

(Continued)

FOREIGN PATENT DOCUMENTS

WO    WO 00/78242    12/2000

(Continued)

OTHER PUBLICATIONS

Hernandez-Zendejas, G., et al., "Percutaneous Selective Radio-Frequency Neuroblation in Plastic Surgery", *Aesth. Plast. Surg.* 18:41-48, 1994.

*Primary Examiner* — Linda Dvorak
*Assistant Examiner* — Amanda Scott
(74) *Attorney, Agent, or Firm* — Levine Bagade Han LLP

(57) ABSTRACT

The invention provides a system and method for achieving the cosmetically beneficial effects of shrinking collagen tissue in the dermis or other areas of tissue in an effective, non-invasive manner using an array of electrodes. Systems described herein allow for improved treatment of tissue. Additional variations of the system include array of electrodes configured to minimize the energy required to produce the desired effect.

20 Claims, 24 Drawing Sheets

(56) References Cited

U.S. PATENT DOCUMENTS

| | | |
|---|---|---|
| 5,569,242 A | 10/1996 | Lax et al. |
| 5,588,960 A | 12/1996 | Edwards et al. |
| 5,599,345 A | 2/1997 | Edwards et al. |
| 5,620,481 A | 4/1997 | Desai et al. |
| 5,643,252 A | 7/1997 | Waner et al. |
| 5,660,836 A | 8/1997 | Knowlton |
| 5,674,267 A | 10/1997 | Mir et al. |
| 5,697,281 A | 12/1997 | Eggers et al. |
| 5,697,909 A | 12/1997 | Eggers et al. |
| 5,702,359 A | 12/1997 | Hofmann et al. |
| 5,755,753 A | 5/1998 | Knowlton |
| 5,769,846 A | 6/1998 | Edwards et al. |
| 5,823,197 A | 10/1998 | Edwards |
| 5,843,078 A | 12/1998 | Sharkey |
| 5,861,002 A | 1/1999 | Desai |
| 5,868,744 A | 2/1999 | Willmen |
| 5,871,469 A | 2/1999 | Eggers et al. |
| 5,891,095 A | 4/1999 | Eggers et al. |
| 5,919,188 A | 7/1999 | Shearon et al. |
| 5,919,219 A | 7/1999 | Knowlton |
| 5,948,011 A | 9/1999 | Knowlton |
| 6,010,500 A | 1/2000 | Sherman et al. |
| 6,024,733 A | 2/2000 | Eggers et al. |
| 6,030,384 A | 2/2000 | Nezhat |
| 6,032,674 A | 3/2000 | Eggers et al. |
| 6,032,675 A | 3/2000 | Rubinsky |
| 6,044,846 A | 4/2000 | Edwards |
| 6,053,909 A | 4/2000 | Shadduck |
| 6,059,820 A | 5/2000 | Baronov |
| 6,066,134 A | 5/2000 | Eggers et al. |
| 6,068,629 A | 5/2000 | Haissaguerre et al. |
| 6,068,653 A | 5/2000 | LaFontaine |
| 6,077,257 A | 6/2000 | Edwards et al. |
| 6,081,749 A | 6/2000 | Ingle et al. |
| 6,117,109 A | 9/2000 | Eggers et al. |
| 6,139,545 A | 10/2000 | Utley et al. |
| 6,142,991 A | 11/2000 | Schatzberger |
| 6,159,194 A | 12/2000 | Eggers et al. |
| 6,222,082 B1 | 4/2001 | Hubbard et al. |
| 6,228,082 B1 | 5/2001 | Baker et al. |
| 6,241,753 B1 | 6/2001 | Knowlton |
| 6,264,652 B1 | 7/2001 | Eggers et al. |
| 6,273,092 B1 | 8/2001 | Nolan |
| 6,273,884 B1 | 8/2001 | Altshuler et al. |
| 6,277,116 B1 | 8/2001 | Utely et al. |
| 6,309,387 B1 | 10/2001 | Eggers et al. |
| 6,377,855 B1 | 4/2002 | Knowlton |
| 6,381,497 B1 | 4/2002 | Knowlton |
| 6,381,498 B1 | 4/2002 | Knowlton |
| 6,383,184 B1 | 5/2002 | Sharkey |
| 6,387,380 B1 | 5/2002 | Knowlton |
| 6,391,023 B1 | 5/2002 | Weber et al. |
| 6,405,090 B1 | 6/2002 | Knowlton |
| 6,405,732 B1 | 6/2002 | Edwards et al. |
| 6,413,255 B1 | 7/2002 | Stern |
| 6,425,912 B1 | 7/2002 | Knowlton |
| 6,461,354 B1 | 10/2002 | Olsen et al. |
| 6,470,216 B1 | 10/2002 | Knowlton |
| 6,482,204 B1 | 11/2002 | Lax et al. |
| 6,496,715 B1 | 12/2002 | Lee et al. |
| 6,511,475 B1 | 1/2003 | Altshuler et al. |
| 6,530,922 B2 | 3/2003 | Cosman et al. |
| 6,558,381 B2 | 5/2003 | Ingle et al. |
| 6,579,288 B1 | 6/2003 | Swanson et al. |
| 6,587,730 B2 | 7/2003 | Bernabei |
| 6,587,731 B1 | 7/2003 | Ingle et al. |
| 6,623,454 B1 | 9/2003 | Eggers et al. |
| 6,632,219 B1 | 10/2003 | Baranov et al. |
| 6,654,636 B1 | 11/2003 | Dev et al. |
| 6,662,054 B2 | 12/2003 | Kreindel et al. |
| 6,673,063 B2 | 1/2004 | Brett |
| 6,678,556 B1 | 1/2004 | Nolan et al. |
| 6,702,808 B1 | 3/2004 | Kreindel |
| 6,706,037 B2 | 3/2004 | Zvuloni et al. |
| 6,723,090 B2 | 4/2004 | Altshuler et al. |
| 6,740,085 B2 | 5/2004 | Hareyama et al. |
| 6,749,607 B2 | 6/2004 | Edwards et al. |
| 6,749,624 B2 | 6/2004 | Knowlton |
| 6,766,202 B2 | 7/2004 | Underwood et al. |
| 6,786,902 B1 | 9/2004 | Rabin et al. |
| 6,836,688 B2 | 12/2004 | Ingle et al. |
| 6,858,025 B2 | 2/2005 | Maurice |
| 6,889,090 B2 | 5/2005 | Kreindel |
| 6,896,672 B1 | 5/2005 | Eggers et al. |
| 6,918,907 B2 | 7/2005 | Kelly et al. |
| 6,920,883 B2 | 7/2005 | Bessette et al. |
| 6,974,450 B2 | 12/2005 | Weber et al. |
| 6,997,923 B2 | 2/2006 | Anderson et al. |
| 7,008,421 B2 | 3/2006 | Daniel et al. |
| 7,018,377 B2 | 3/2006 | Hood et al. |
| 7,022,121 B2 | 4/2006 | Stern et al. |
| 7,077,842 B1 | 7/2006 | Cosman |
| 7,101,387 B2 | 9/2006 | Garabedian et al. |
| 7,141,049 B2 | 11/2006 | Stern et al. |
| 7,167,757 B2 | 1/2007 | Ingle et al. |
| 7,278,991 B2 | 10/2007 | Morris et al. |
| 7,331,953 B2 | 2/2008 | Manstein et al. |
| 7,763,018 B2 | 7/2010 | DeCarlo et al. |
| 8,142,426 B2 | 3/2012 | Knopp et al. |
| 8,273,080 B2 | 9/2012 | Mehta |
| 8,419,726 B2 | 4/2013 | Mehta |
| 2001/0025190 A1 | 9/2001 | Weber et al. |
| 2002/0077628 A1 | 6/2002 | Burbank et al. |
| 2002/0120260 A1 | 8/2002 | Morris et al. |
| 2002/0120261 A1 | 8/2002 | Morris et al. |
| 2002/0128641 A1 | 9/2002 | Underwood et al. |
| 2002/0133149 A1 | 9/2002 | Bessette |
| 2002/0156471 A1 | 10/2002 | Stern et al. |
| 2003/0032950 A1 | 2/2003 | Altshuler et al. |
| 2003/0109787 A1 | 6/2003 | Black |
| 2003/0109860 A1 | 6/2003 | Black |
| 2003/0130655 A1 | 7/2003 | Woloszko et al. |
| 2003/0212394 A1 | 11/2003 | Pearson et al. |
| 2003/0216719 A1 | 11/2003 | Debenedictis et al. |
| 2004/0082940 A1 | 4/2004 | Black et al. |
| 2004/0162474 A1 | 8/2004 | Kiser et al. |
| 2004/0193238 A1 | 9/2004 | Mosher et al. |
| 2004/0204728 A1 | 10/2004 | Haefner |
| 2004/0267251 A1 | 12/2004 | Sutton |
| 2005/0049582 A1 | 3/2005 | DeBenedictis et al. |
| 2005/0055073 A1 | 3/2005 | Weber |
| 2005/0101945 A1 | 5/2005 | Sakurai et al. |
| 2005/0119654 A1 | 6/2005 | Swanson et al. |
| 2005/0137662 A1 | 6/2005 | Morris et al. |
| 2005/0222555 A1 | 10/2005 | Manstein et al. |
| 2005/0222565 A1 | 10/2005 | Manstein |
| 2005/0273092 A1 | 12/2005 | G. et al. |
| 2006/0004347 A1 | 1/2006 | Altshuler et al. |
| 2006/0047281 A1 | 3/2006 | Kreindel |
| 2006/0058712 A1 | 3/2006 | Altshuler et al. |
| 2006/0089688 A1 | 4/2006 | Panescu |
| 2006/0106375 A1 | 5/2006 | Werneth et al. |
| 2006/0122668 A1 | 6/2006 | Anderson et al. |
| 2006/0155266 A1 | 7/2006 | Manstein et al. |
| 2006/0217788 A1 | 9/2006 | Herron et al. |
| 2007/0073308 A1 | 3/2007 | Anderson et al. |
| 2007/0093798 A1 | 4/2007 | DeBenedictis et al. |
| 2007/0129714 A1 | 6/2007 | Elkins et al. |
| 2007/0142885 A1 | 6/2007 | Hantash et al. |
| 2007/0179481 A1 | 8/2007 | Frangineas et al. |
| 2007/0265606 A1 | 11/2007 | DeBenedictis et al. |
| 2008/0009842 A1 | 1/2008 | Manstein et al. |
| 2008/0015555 A1 | 1/2008 | Manstein et al. |
| 2008/0021442 A1 | 1/2008 | Manstein et al. |
| 2008/0058783 A1 | 3/2008 | Altshuler et al. |
| 2008/0058784 A1 | 3/2008 | Manstein et al. |
| 2008/0082090 A1 | 4/2008 | Manstein |
| 2008/0091182 A1 | 4/2008 | Mehta |
| 2008/0132886 A1 | 6/2008 | Cohen et al. |
| 2008/0172047 A1 | 7/2008 | Altshuler et al. |
| 2008/0183162 A1 | 7/2008 | Altshuler et al. |
| 2008/0214988 A1 | 9/2008 | Altshuler et al. |
| 2008/0294150 A1 | 11/2008 | Altshuler et al. |
| 2008/0306471 A1 | 12/2008 | Altshuler et al. |

(56) References Cited

U.S. PATENT DOCUMENTS

| | | |
|---|---|---|
| 2009/0069741 A1 | 3/2009 | Altshuler et al. |
| 2009/0118720 A1 | 5/2009 | Black et al. |
| 2010/0145321 A1 | 6/2010 | Altshuler et al. |
| 2011/0046615 A1 | 2/2011 | Manstein |
| 2012/0143270 A1 | 6/2012 | Mehta |
| 2012/0226336 A1 | 9/2012 | Knopp et al. |

FOREIGN PATENT DOCUMENTS

| | | |
|---|---|---|
| WO | WO 01/49194 | 7/2001 |
| WO | WO 02/053050 | 7/2002 |
| WO | WO 2004/086947 | 10/2004 |
| WO | WO 2005/107848 C1 | 4/2005 |
| WO | WO 2005/096979 | 10/2005 |
| WO | WO 2005/096981 | 10/2005 |
| WO | WO 2005/107848 | 11/2005 |
| WO | WO 2006/127467 | 11/2006 |

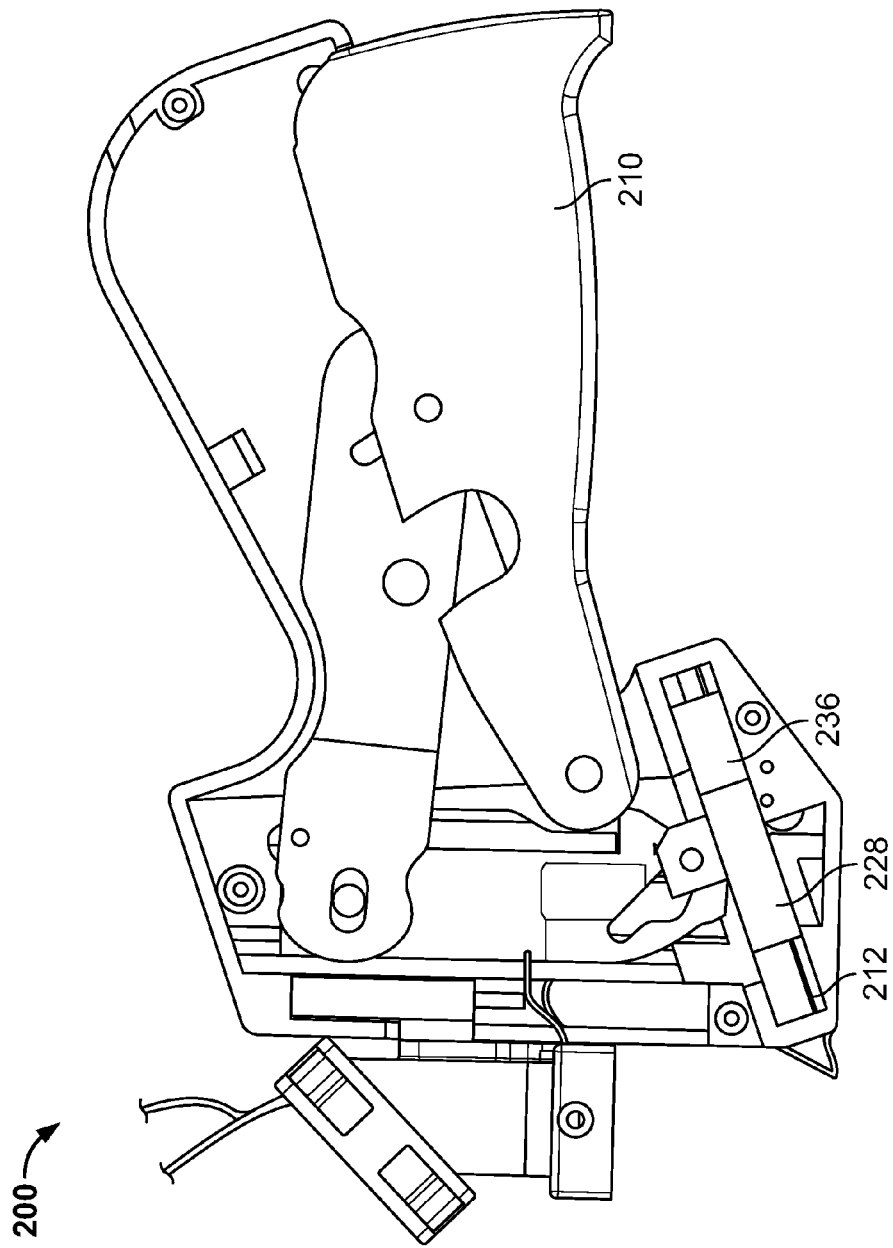

METHODS AND DEVICES FOR TREATING TISSUE

CROSS-REFERENCE TO RELATED APPLICATIONS

This application is a continuation of U.S. application Ser. No. 11/676,235 filed Feb. 16, 2007, (now U.S. Pat. No. 8,142, 426), which claims benefit the benefit U.S. Provisional Application No. 60/829,607 filed Oct. 16, 2006, the contents of both of which are incorporated by reference herein in their entirety for all purposes.

BACKGROUND OF THE INVENTION

The systems and method discussed herein treat tissue in the human body. In a particular variation, systems and methods described below treat cosmetic conditions affecting the skin of various body parts, including face, neck, and other areas traditionally prone to wrinkling, lines, sagging and other distortions of the skin.

Exposure of the skin to environmental forces can, over time, cause the skin to sag, wrinkle, form lines, or develop other undesirable distortions. Even normal contraction of facial and neck muscles, e.g. by frowning or squinting, can also over time form furrows or bands in the face and neck region. These and other effects of the normal aging process can present an aesthetically unpleasing cosmetic appearance.

Accordingly, there is well known demand for cosmetic procedures to reduce the visible effects of such skin distortions. There remains a large demand for "tightening" skin to remove sags and wrinkles especially in the regions of the face and neck.

One method surgically resurfaces facial skin by ablating the outer layer of the skin (from 200 µm to 600 µm), using laser or chemicals. In time, a new skin surface develops. The laser and chemicals used to resurface the skin also irritate or heat the collagen tissue present in the dermis. When irritated or heated in prescribed ways, the collagen tissue partially dissociates and, in doing so, shrinks. The shrinkage of collagen also leads to a desirable "tightened" look. Still, laser or chemical resurfacing leads to prolonged redness of the skin, infection risk, increased or decreased pigmentation, and scarring.

Lax et al. U.S. Pat. No. 5,458,596 describes the use of radio frequency energy to shrink collagen tissue. This cosmetically beneficial effect can be achieved in facial and neck areas of the body in a minimally intrusive manner, without requiring the surgical removal of the outer layers of skin and the attendant problems just listed.

Utely et al. U.S. Pat. No. 6,277,116 also teaches a system for shrinking collagen for cosmetically beneficial purposes by using an electrode array configuration.

However, areas of improvement remain with the previously known systems. In one example, fabrication of an electrode array may cause undesired cross-current paths forming between adjacent electrodes resulting in an increase in the amount of energy applied to tissue.

In another example, when applying the array to tissue, the medical practitioner experiences a "bed-of-nails". In other words, the number of electrodes and their configuration in the array effectively increases the total surface area of the electrode array. The increase in effective surface area then requires the medical practitioner to apply a greater force to the electrode array in order to penetrate tissue. Such a drawback may create collateral damage as one or more electrode may be placed too far within the skin. Additionally, the patient may experience the excessive force as the medical practitioner increases the applied force to insert the array within tissue.

Thermage, Inc. of Hayward Calif. also holds patents and sells devices for systems for capacitive coupling of electrodes to deliver a controlled amount of radiofrequency energy. This controlled delivery of RF energy creates an electric field that generates "resistive heating" in the skin to produce cosmetic effects while cooling the epidermis to prevent external burning of the epidermis.

In such systems that treat in a non-invasive manner, generation of energy to produce a result at the dermis results in unwanted energy passing to the epidermis. Accordingly, excessive energy production creates the risk of unwanted collateral damage to the skin.

In view of the above, there remains a need for an improved energy delivery system. Such systems may be applied to create improved electrode array delivery system for cosmetic treatment of tissue. In particular, such an electrode array may provide deep uniform heating by applying energy to tissue below the epidermis to causes deep structures in the skin to immediately tighten. Over time, new and remodeled collagen may further produce a tightening of the skin, resulting in a desirable visual appearance at the skin's surface.

SUMMARY OF THE INVENTION

The invention provides improved systems and methods of systems and methods of achieving the cosmetically beneficial effects of using energy to shrink collagen tissue in the dermis in an effective manner that prevents the energy from affecting the outer layer of skin.

One aspect of the invention provides systems and methods for applying electromagnetic energy to skin. The systems and methods include a carrier and an array of electrodes on the carrier, which are connectable to a source of electromagnetic energy to apply the electromagnetic energy. The devices and methods described herein can also be used to treat tissue masses such as tumors, varicose veins, or other tissue adjacent to the surface of tissue.

The devices and methods described herein may provide electrode arrays that penetrate tissue at an oblique angle or at a normal angle as discussed below. In addition, in those variations where the electrode array enters at an oblique angle, the device may include a cooling surface that directly cools the surface area of tissue adjacent to the treated region of tissue. The cooling methods and apparatus described herein may be implemented regardless of whether the electrodes penetrate at an oblique angle or not.

According to this aspect of the invention, a faceplate on the carrier or treatment unit covers the array of electrodes. Faceplate can be a non-conducting material and may or may not conform to the outer surface of tissue.

An interior chamber is formed behind the faceplate and contains an electrode plate. The electrode plate can move within the chamber to allow movement of the electrodes through openings in the faceplate. It is noted however, that variations of the invention may or may not have a faceplate and/or an electrode plate.

Methods described herein include methods for applying energy to tissue located beneath a surface layer of the tissue by providing an energy transfer unit having a faceplate with a plurality of openings and a plurality of electrodes moveable through the faceplate. In operation a medical practitioner can place the faceplate in contact with the surface layer of tissue then draw and maintain the surface layer of tissue against the openings in the faceplate. Subsequently, or simultaneously to this act, the medical practitioner can advance the electrodes through the surface tissue and into the tissue and apply energy with a portion of the electrode beneath the skin to create a thermal injury to tissue beneath the skin.

The number of openings may match the number of electrodes. Alternatively, there may be additional openings in the treatment unit to maintain a vacuum with the tissue and/or allow movement of the electrodes within the chamber.

Variations of the invention include movement of the electrodes by use of a spring. The spring provides a spring force to move the electrodes at a velocity that allows for easier insertion of the electrode array into tissue.

Alternatively, or in combination, the electrodes may be coupled to an additional source of energy that imparts vibration in the electrodes (e.g., an ultrasound energy generator). The same energy source may be used to generate the thermal effect in the dermis.

The methods and devices described herein may also use features to facilitate entry of the electrodes into tissue. For example, the surface tissue may be placed in traction prior to advancing electrodes through the surface tissue. The electrodes can comprise a curved shape. Where advancing the curved electrodes through tissue comprises rotating the electrodes into tissue.

The power supply for use with the systems and methods described herein may comprise a plurality of electrode pairs, each electrode pair comprising a mono-polar or bi-polar configuration. Each electrode pair of the system may be coupled to an independent channel of a power supply or independent power supplies. Such configurations permit improved controlled delivery of energy to the treatment site.

Another variation that controls delivery of energy may include spacing where each electrode pair at a sufficient distance from an adjacent electrode pair to minimize formation of a cross-current path between adjacent electrode pairs. Moreover, the independent power supply can be configured to energize adjacent electrode pairs at different times.

Devices according to the principles of the present invention include an electrode array for treating a dermis layer of tissue, the array comprising a faceplate comprising a plurality of openings, a plurality of electrode pairs each pair comprising an active and a return electrode, where the electrode pairs extend through openings in the faceplate, at least one electrode plate carrying the plurality of electrode pairs, where the electrode plate and face plate are moveable relative to each other to allow for axial movement of the electrode pairs through the openings.

It is expressly intended that, wherever possible, the invention includes combinations of aspects of the various embodiments described herein or even combinations of the embodiments themselves.

BRIEF DESCRIPTION OF THE DRAWINGS

FIGS. 9A to 9D show another variation of an electrode device with a cooling system that can be placed adjacent to the electrodes;

DESCRIPTION OF THE PREFERRED EMBODIMENT

The systems and method discussed herein treat tissue in the human body. In one variation, the systems and methods treat cosmetic conditions affecting the skin of various body parts, including face, neck, and other areas traditionally prone to wrinkling, lines, sagging and other distortions of the skin. The methods and systems described herein may also have application in other surgical fields apart from cosmetic applications.

Figure 1:
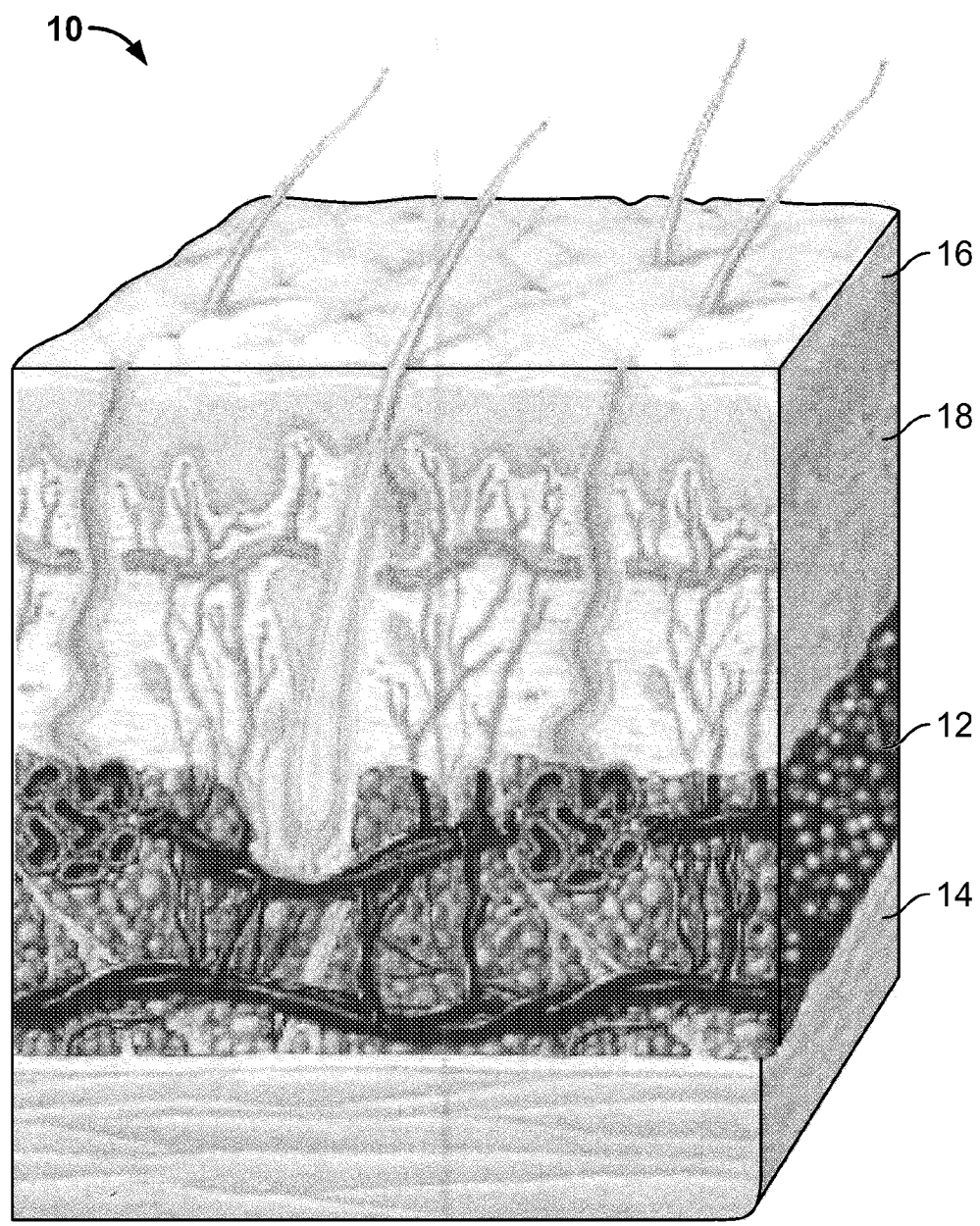
FIG. 1 shows a representative sectional view of skin and underlying subcutaneous tissue.

As FIG. 1 shows, the skin 10 covers subcutaneous tissue 12 and muscle tissue 14 of within the body. In the face and neck areas, the skin 10 measures about 2 mm in cross section.

The skin 10 includes an external, non-vascular covering called the epidermis 16. In the face and neck regions, the epidermis measures about 100 μm in cross section. The skin 10 also includes a dermis 18 layer that contains a layer of vascular tissue. In the face and neck regions, the dermis 18 measures about 1900 μm in cross section.

The dermis 18 includes a papillary (upper) layer and a reticular (lower) layer. Most of the dermis 18 comprises collagen fibers. However, the dermis also includes various hair bulbs, sweat ducts, and other glands. The subcutaneous tissue 12 region below the dermis 18 contains fat deposits as well as vessels and other tissue.

In most cases, when applying cosmetic treatment to the skin, it is desirable to deliver energy the dermis layer rather than the epidermis, the subcutaneous tissue region 12 or the muscle 14 tissue. In fact, delivery of energy to the subcutaneous tissue region 12 or muscle 14 may produce pockets or other voids leading to further visible imperfections in the skin of a patient.

The application of heat to the fibrous collagen structure in the dermis 18 causes the collagen to dissociate and contract along its length. It is believed that such disassociation and contraction occur when the collagen is heated to about 65 degree. C. The contraction of collagen tissue causes the dermis 18 to reduce in size, which has an observable tightening effect. As the collagen contacts, wrinkles, lines, and other distortions become less visible. As a result, the outward cosmetic appearance of the skin 10 improves. Furthermore, the eventual wound healing response may further cause additional collagen production. This latter effect may further serve to tighten the skin 10.

Figure 2A:
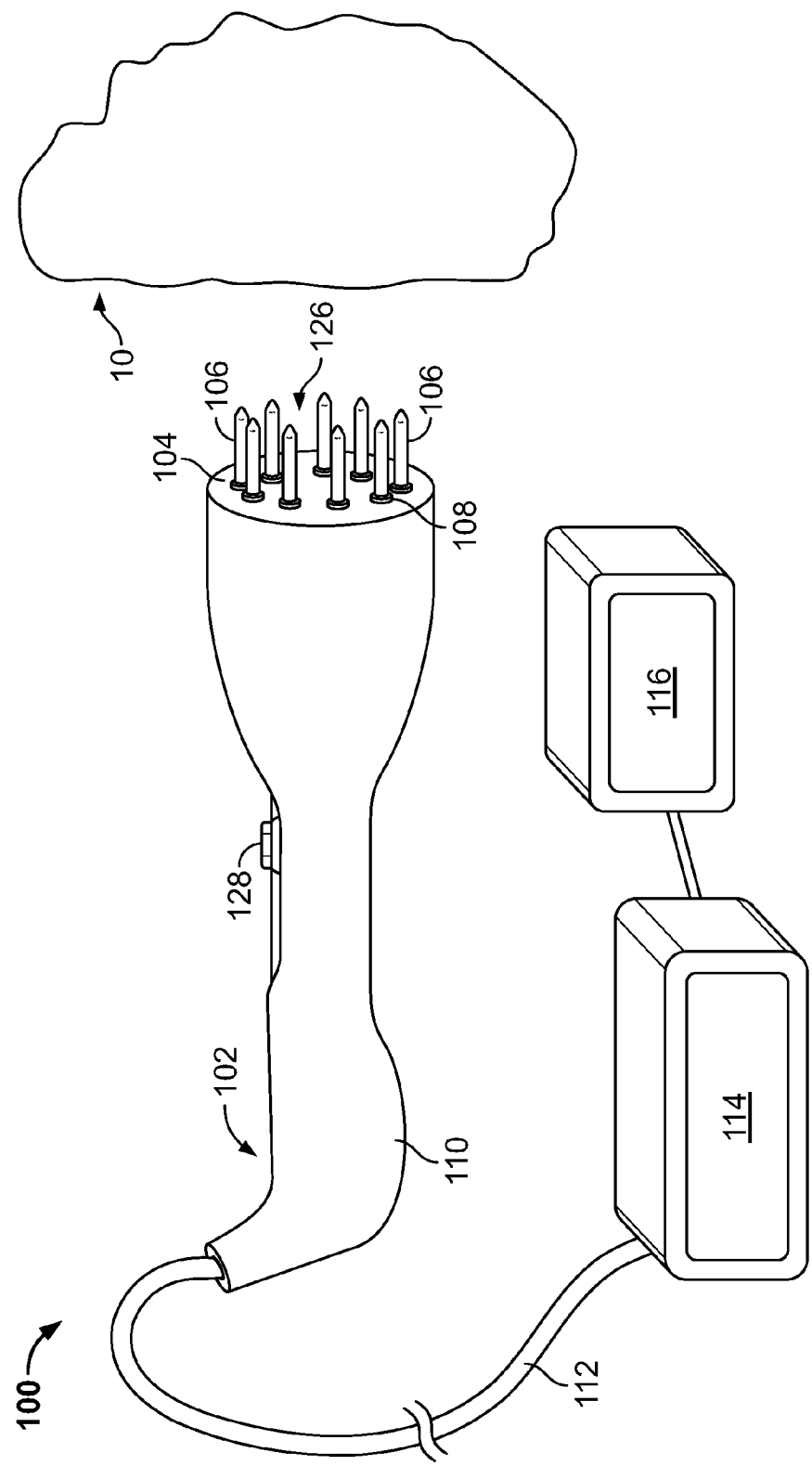
FIG. 2A shows a sample variation of a system according to the principles of the invention.

FIG. 2A illustrates a variation of a treatment system according the principles described herein. The treatment system 100 generally includes a treatment unit 102 having a hand-piece 110 (or other member/feature that allows for manipulation of the system to treat tissue 10). The treatment unit 102 shown includes a faceplate 104 having a plurality of electrodes 106 (generally formed in an array) that extend from openings 108 in the faceplate 104. The devices may comprise electrode arrays of only a single electrode pair up to considerably larger arrays. Currently, the size of the array is determined by the target region that is intended for treatment. For example, a treatment unit 102 designed for relatively small treatment areas may only have a single pair of electrodes. On the other hand, a treatment unit 102 designed for use on the cheek or neck may have up to 10 electrode pairs. However, estimates on the size of the electrode array are for illustrative purposes only. In addition, the electrodes on any given array may be the same shape and profile. Alternatively, a single array may have electrodes of varying shapes, profiles, and/or sizes depending upon the intended application.

The electrodes 106 can be fabricated from any number of materials, e.g., from stainless steel, platinum, and other noble metals, or combinations thereof. Additionally, the electrode may be placed on a non-conductive member (such as a polymeric member). In any case, the electrode 106 may be fastened to the electrode plate by various means, e.g., by adhesives, by painting, or by other coating or deposition techniques.

Additionally, the treatment unit 102 may or may not include an actuator 128 for driving the electrode array 126 from the faceplate 104. Alternative variations of the system 100 include actuators driven by the control system 114.

The number of electrodes 106 in the array may vary as needed for the particular application. Furthermore, the array defined by the electrodes 106 may have any number of shapes or profiles depending on the particular application. As described in additional detail herein, in those variations of the system 100 intended for skin resurfacing, the length of the electrodes 106 is generally selected so that the energy delivery occurs in the dermis layer of the skin 10 while the spacing of electrodes 106 may be selected to minimize flow of current between adjacent pairs of electrodes.

When treating the skin, it is believed that the dermis should be heated to a predetermined temperature condition, at or about 65 degree C., without increasing the temperature of the epidermis beyond 47 degree C. Since the active area of the electrode designed to remain beneath the epidermis, the present system applies energy to the dermis in a targeted, selective fashion, to dissociate and contract collagen tissue. By attempting to limit energy delivery to the dermis, the configuration of the present system also minimizes damage to the epidermis.

The system 10 also includes an energy supply unit 114 coupled to the treatment unit 102 via a cable 112 or other means. The energy supply unit 114 may contain the software and hardware required to control energy delivery. Alternatively, the CPU, software and other hardware control systems may reside in the hand piece 110 and/or cable 112. It is also noted that the cable 112 may be permanently affixed to the supply unit 114 and/or the treatment unit 102. The energy supply unit may be a RF energy unit. Additional variations of energy supply units may include power supplies to provide thermal energy, ultrasound energy, laser energy, and infrared energy.

The energy supply unit 114 may also include an input/output (I/O) device that allows the physician to input control and processing variables, to enable the controller 114 to generate appropriate command signals. The I/O device can also receive real time processing feedback information from one or more sensors 98 associated with the device, for processing by the controller 114, e.g., to govern the application of energy and the delivery of processing fluid. The I/O device may also include a display 54, to graphically present processing information to the physician for viewing or analysis.

In some variations, the system 100 may also include an auxiliary unit 116 (where the auxiliary unit may be a vacuum source, fluid source, ultrasound generator, medication source, etc.) Although the auxiliary unit is shown to be connected to the energy supply, variations of the system 100 may include one or more auxiliary units 116 where each unit may be coupled to the power supply 114 and/or the treatment unit 102.

Figure 2B:
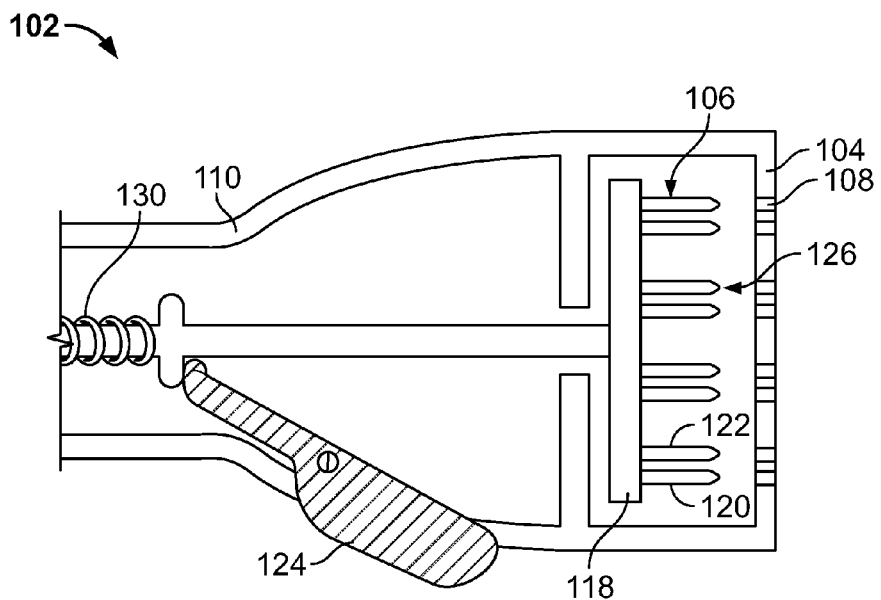
FIG. 2B illustrates a partial cross-sectional view of an exemplary treatment unit where the electrode array is retained proximal to a faceplate of the device.

FIG. 2B illustrates a cross sectional view of a variation of a treatment unit 102 according to the systems described herein. As shown, the treatment unit 102 includes the hand piece body 110 that houses the electrode array 126 on an electrode plate 118. Naturally, the hand piece 110 or treatment unit 102 may have any shape that accommodates ease of use.

FIG. 2B also shows the electrode array 126 being withdrawn behind the faceplate 104. In the illustrated variation, the treatment unit 102 includes a spring release lever or trigger 124. As described below, the spring release trigger 124 can be used to actuate a spring 130 (a coiled spring or other similar structure) to drive the electrode array 126 through openings 108 in the faceplate 104. Driving the electrode array 126 with the spring-force increases the force of the electrodes as they approach tissue and facilitates improved penetration of the tissue by the electrodes. Although the inventive system may not include such a spring force, the absence of such a feature may require the medical practitioner to apply excessive force to the entire treatment unit 102 when trying to insert the electrodes due to a "bed-of-nails" effect.

Figure 2C:
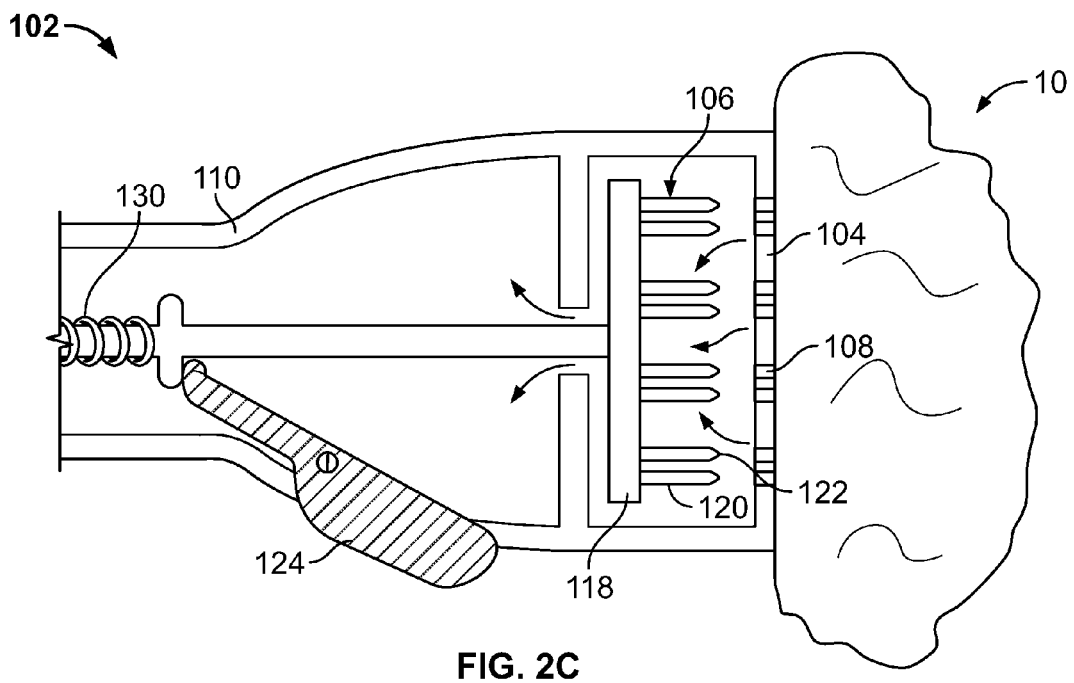
FIGS. 2C-2D respectively illustrates a partial cross sectional view of an exemplary treatment unit after tissue is drawn against the unit and the unit after the electrodes deploy into tissue.

FIG. 2C illustrates the treatment unit 102 as it is placed against tissue 10. In this variation, a vacuum source (not shown) may be applied to the unit 102 to draw the tissue 10 against the faceplate 104. Typically, the vacuum pulls the tissue in through the openings 108 on the faceplate 104. Variations of the device include additional openings in the faceplate in addition to openings that allow passage of the electrodes. This latter configuration permits application of a vacuum as the electrodes penetrate the tissue.

By drawing tissue against the device or faceplate, the medical practitioner may better gauge the depth of the treatment. For example, given the relatively small sectional regions of the epidermis, dermis, and subcutaneous tissue, if a device is placed over an uneven contour of tissue, one electrode pair may be not be placed at the sufficient depth. Accordingly, application of energy in such a case may cause a burn on the epidermis. Therefore, drawing tissue to the faceplate of the device increases the likelihood of driving the electrodes to a uniform depth in the tissue.

Although not shown, the electrode plate 118 may contain apertures or other features to allow distal movement of the plate 118 and electrodes 106 during the application of a vacuum.

Figure 2D:
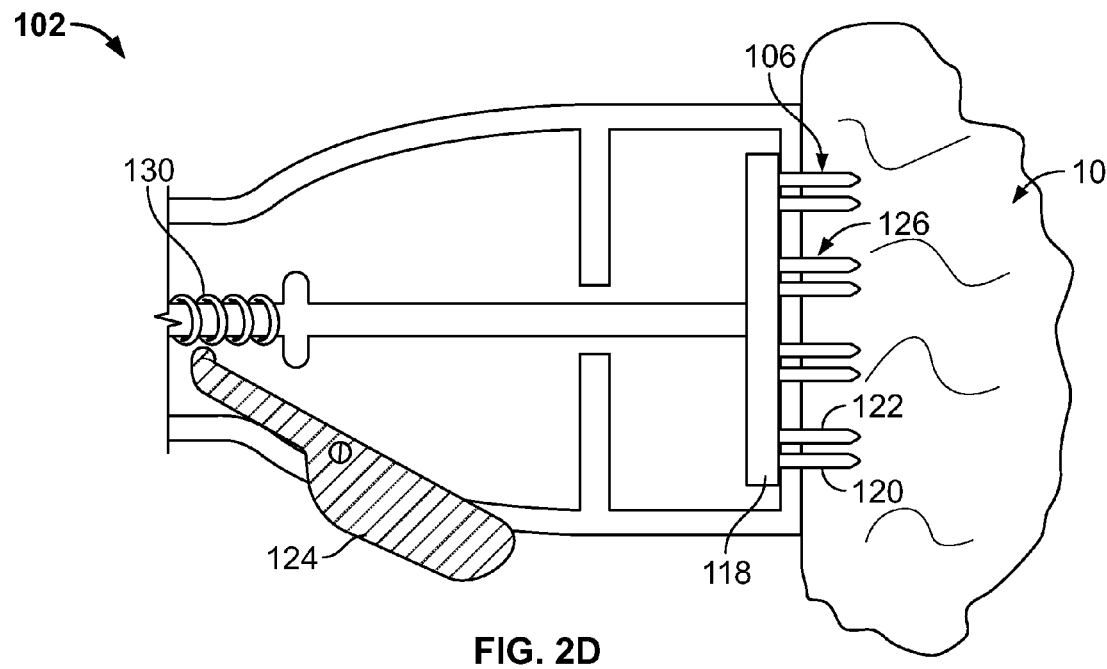

FIG. 2D illustrates deployment of the electrode array 126 into the tissue 10. Although not shown, in variations of the device suited for cosmetic applications, the length of the electrodes 106 will be chose to place the active region of the electrode (i.e., the region that conducts electricity) within the dermis. Again, the depth of the electrodes may vary depending upon the region of the body intended for treatment. In one variation, the electrodes 106 may be driven into the tissue as far as possible to ensure complete contact between the faceplate 104 and the surface of the skin. Subsequently, the electrode may be withdrawn a predetermined distance to place the active portion of the electrode in the proper location.

Figure 2E:
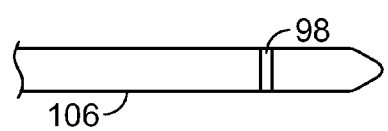
FIG. 2E illustrates a variation of a sensor disposed on an electrode.

FIG. 2E illustrates an example of an electrode 106 having a sensor 98. The sensor may be any device that monitors temperature of the tissue, impedance, or other characteristic. Additionally, more than one sensor 98 may be used on a single electrode, on an electrode array, on the faceplate or any combination thereof.

In variations of the present system, the electrodes 106 can be configured to individually rotate, vibrate (e.g., via ultrasonic energy), or cycle in an axial direction, where such actions are intended to lower the overall insertion force required by the medical practitioner to place the electrodes within tissue.

The electrodes 106 are arranged in a pair configuration. In a bi-polar configuration one electrode 120 serves a first pole, while the second electrode 122 serves as the second pole (it is also common to refer to such electrodes as the active and return electrodes). The spacing of electrode pairs 106 is sufficient so that the pair of electrodes 120, 122 is able to establish a treatment current path therebetween for the treatment of tissue. However, adjacent electrode pairs 106 will be spaced sufficiently to minimize the tendency of current flowing between the adjacent pairs. Typically, each electrode pair 106 is coupled to a separate power supply or to a single power supply having multiple channels for each electrode pair.

The benefit of such a configuration is that, when compared to conventional treatments, the amount of power required to induce heating in the target tissue is much reduced. For example, because the electrodes are spaced to provide heating across the electrode pairs at the target tissue, each channel of the system may provide 1 watt of energy to produce the desired temperature increase at the site. In contrast, if a treatment system delivered energy over the entire electrode array, a much greater amount of energy is required to generate the desired temperature over the larger surface area of tissue. Moreover, the energy demand is less because the treatment applies energy directly to the target tissue rather than though additional layers of tissue.

In one variation of the device, it is believed that a desirable spacing of the first and second electrode poles is between 1 and 3 mm, while a desirable spacing of electrode pairs is between 5 and 6 mm. In one example, the described configuration allowed for each independent channel to deliver no more than 1 watt to deliver acceptable tissue treatment results. Obviously, the power supply may be configured to deliver greater amounts of energy as needed depending on the application.

Figure 2F:
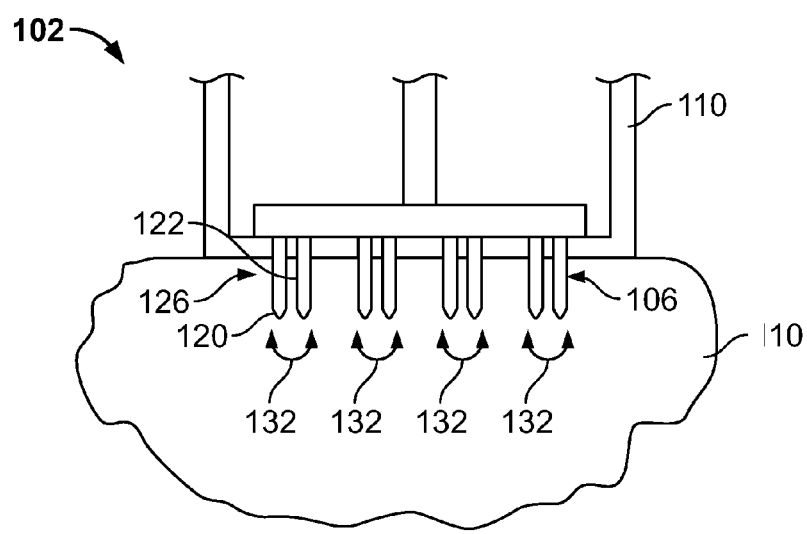
FIG. 2F shows an example of spacing of electrode pairs in the electrode array to minimize current flow between adjacent electrode pairs.

FIG. 2F illustrates the electrode array 126 when deployed within tissue 10. As noted above, variations of the device include electrode pairs 120, 122 provided in a bi-polar configuration where each pair is coupled to a separate power supply or separate channel of a power supply. As shown, this configuration permits flow of current 132 between the two electrodes in the electrode pair rather than between adjacent pairs. Again, the invention is not limited to such a configuration and may be monopolar, and/or have electrode spacing that permits flow of current between several electrodes on the electrode array.

The ability to control each electrode pair on a separate channel from the power supply provides additional benefits based on the impedance or other characteristic of the tissue being treated. For example, each electrode pair may include a thermocouple to separately monitor each treatment site; the duration of the energy treatment may be controlled depending on the characteristics of the surrounding tissue; selective electrode pairs may be fired rather than all of the electrode pairs firing at once (e.g., by firing electrode pairs that are located on opposite ends of the electrode plate one can further minimize the chance that a significant amount of current flows between the separate electrode pairs.) Naturally, a number of additional configurations are also available depending on the application. Additional variations of the device may include electrode pairs that are coupled to a single channel of a power supply as well.

The present systems may deliver energy based upon sensing tissue temperature conditions as a form of active process feedback control. Alternatively, the systems may monitor changes in impedance of the tissue being treated and ultimately stop the treatment when a desired value is obtained. Yet another mode of energy delivery is to provide a total maximum energy over a duration of time.

As noted herein, temperature or other sensing may be measured beneath the epidermis in the dermis region. Each probe or electrode may include a sensor or the sensor may be placed on a structure that penetrates the tissue but does not function as an energy delivery electrode. In yet another variation, the sensors may be a vertically stacked array of sensors to provide data along a depth or length of tissue.

Figure 3A:
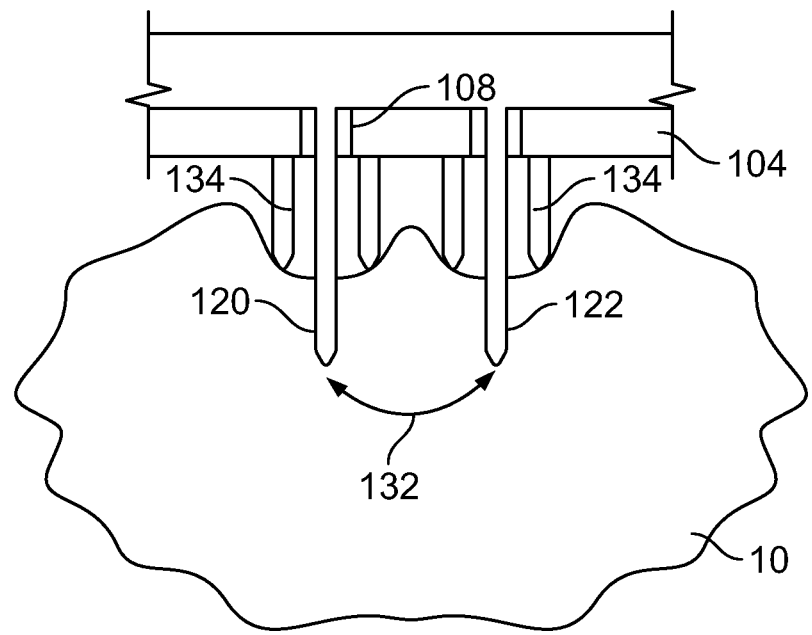
FIGS. 3A to 3B show variations of introducer members that assist in placing electrodes within tissue.

FIG. 3A illustrates an aspect for use with the variations of the devices described herein. In this example, the electrodes 120, 122 include an introducer member 134 that places tissue 10 in a state of tension (also called "traction"). In this variation the introducer 134 is located about each opening 108 in the faceplate 104. However, alternate variations of the device include introducer members placed directly on the electrode.

As shown, once the introducer member 134 engages tissue 10, the tissue first elastically deforms as shown. Eventually, the tissue can no longer deflect and is placed in traction by the introducer members 134. As a result, the electrodes 120, 122 more readily penetrate the tissue.

Figure 3B:
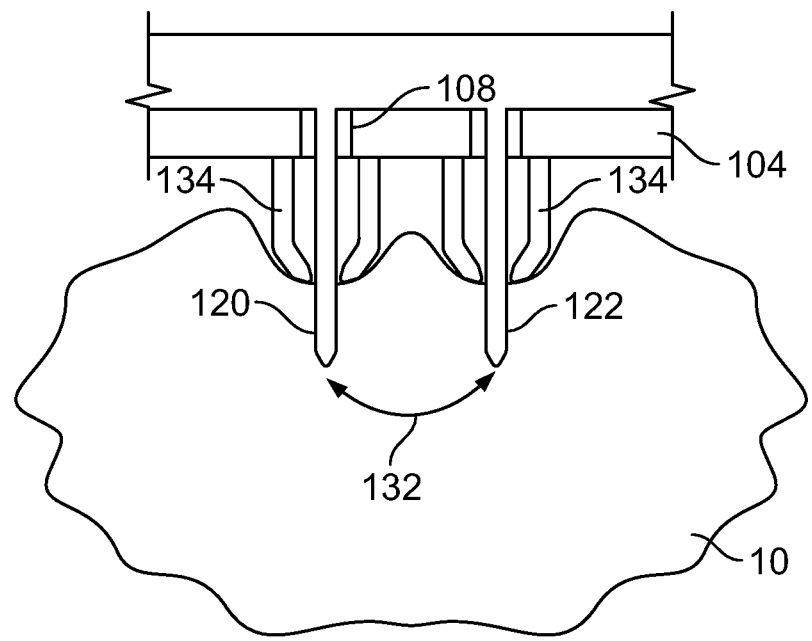

FIG. 3B illustrates another variation of the introducer member 134 that is tapered inwards toward the electrodes so that the opening at the distal end closely fits around the electrode.

In those variations of systems according to the present invention, if the electrodes engage the tissue without the introducer members, then the electrodes themselves may cause plastic deformation of the surface tissue. Such an occurrence increases the force a medical practitioner must apply to the device to deploy the electrodes in tissue.

Figure 4A:
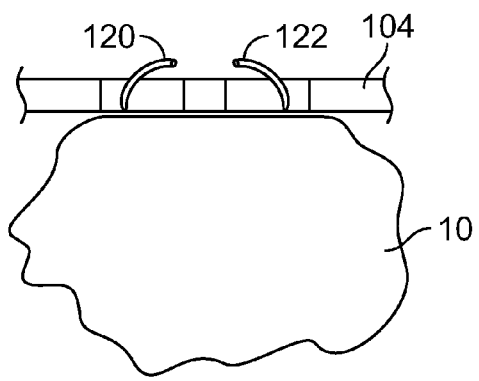
FIGS. 4A to 4C show variations of curved electrodes that pivot or rotate into tissue.

FIG. 4A shows another variation of an aspect for use with variations of the inventive device where the electrodes 120, 122 in the array have a curved or arcuate profile. When actuated, the electrodes 120, 122 rotate into the tissue 10. Such a configuration may rely on a cam type mechanism (e.g., where the electrode plate and electrode rely on a cam-follower type motion to produce rotation of the electrodes).

Figure 4B:
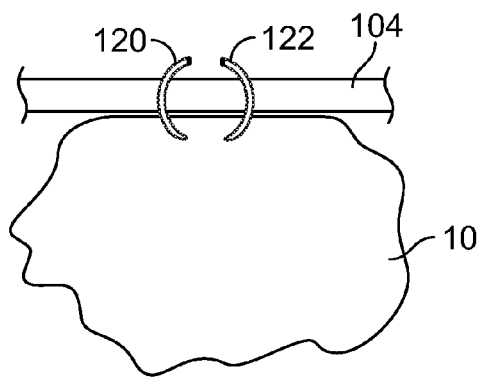

The electrodes 120, 122 may have a curved shape similar to that of suture needles, and/or may be fabricated from a shape memory alloy that is set in a desired curve. As shown in FIG. 4B, as the electrodes 120, 122 rotate into tissue, the rotational movement substantially causes a transverse force within the tissue rather than a normal force to the tissue. Accordingly, there is less tissue deformation as the electrodes penetrate the tissue allowing for ease of insertion.

FIG. 4B illustrates the first and second electrodes 120,122 within tissue. The depth of insertion of these electrodes may be controlled by selecting a proper combination of electrode length and radius of curvature.

Figure 4C:
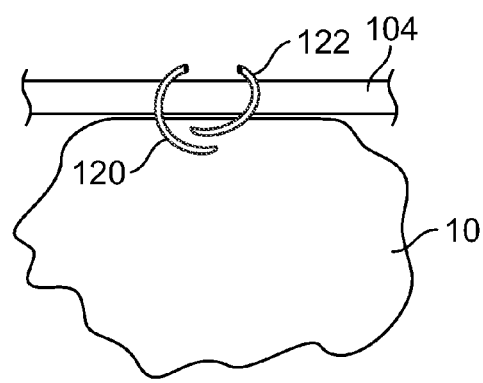

FIG. 4C illustrates another variation of curved electrodes. In this variation, the electrodes may be configured to overlap. Such overlap results in the active electrode area being close in proximity to better control the current path between electrodes.

Figure 5A:
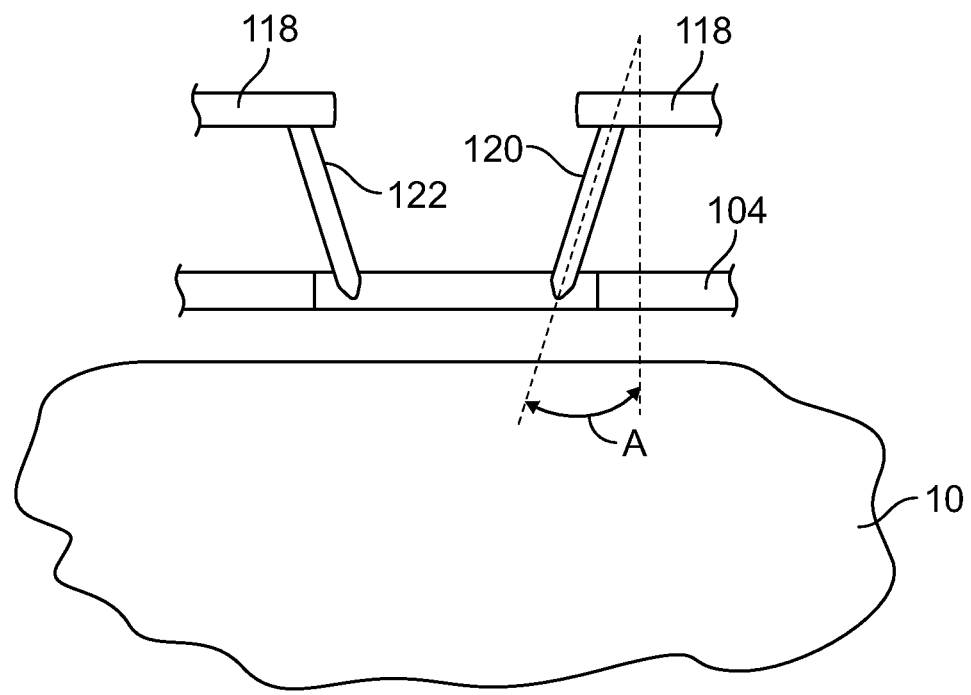
FIGS. 5A to 5D show variations of electrodes placed at oblique angles.
Figure 5B:
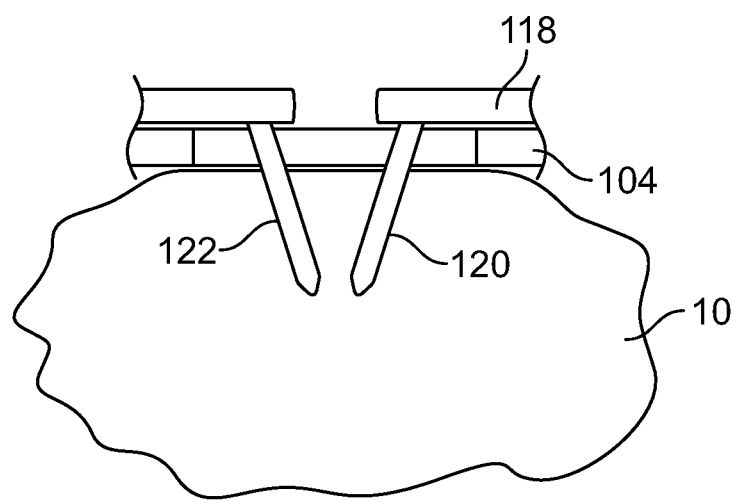

FIG. 5A shows another electrode configuration for use with variations of the inventive device. As illustrated, the electrodes 120, 122 may be placed at an oblique angle A relative to the face plate 104 or treatment unit 102. FIG. 5A illustrates the condition as the electrodes 120, 122 approach the tissue 10. FIG. 5B shows the electrodes 120, 122 being advanced towards each other as are placed in tissue 10. The angle of the electrodes 120, 122 creates a lateral or transverse force on the tissue 10 that serves to place a portion of the tissue in a state of traction.

Figure 5C:
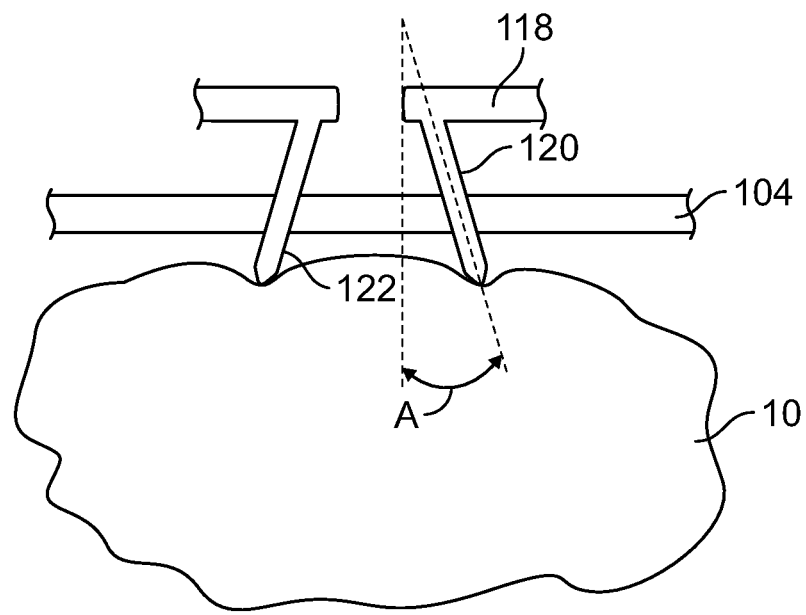
Figure 5D:
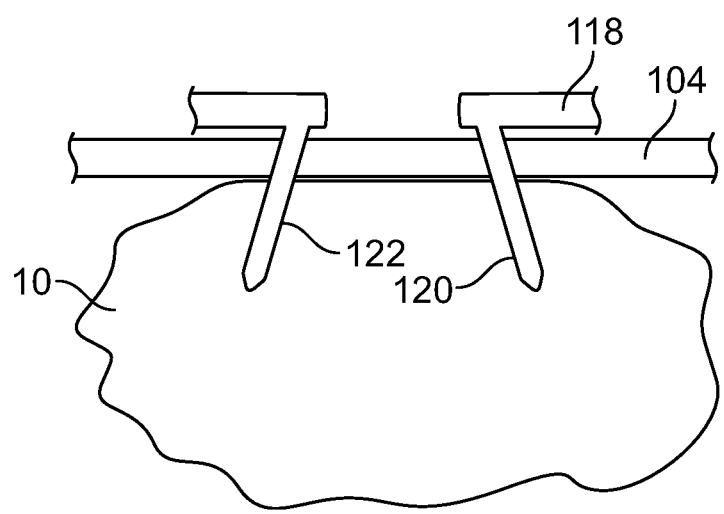

FIG. 5C shows a variation in which the electrodes 120, 122 approach the tissue at an oblique angle A but where the electrodes are directed away from one another. Again, this configuration provides an opposing force on the tissue 10 between the electrodes as the electrodes 120, 122 penetrate the tissue. FIG. 5D shows the electrodes after they are inserted. Again, such a configuration reduces the force required to place the electrodes within tissue.

In the above configuration, it may be necessary to have one or more electrode plates 104 as an electrode moves along two or more dimensions. However, various additional configurations may be employed to produce the desired effects.

Figure 6A:
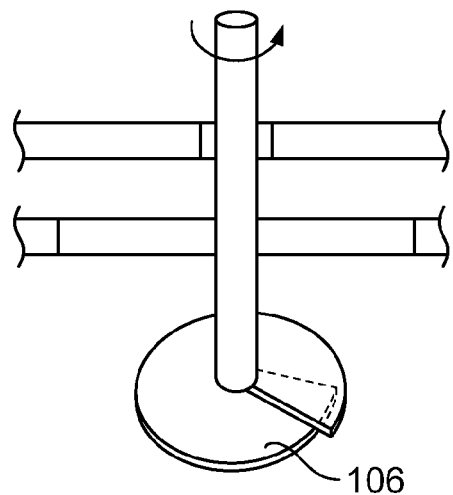
FIGS. 6A to 6C show additional variations of electrode configurations.
Figure 6B:
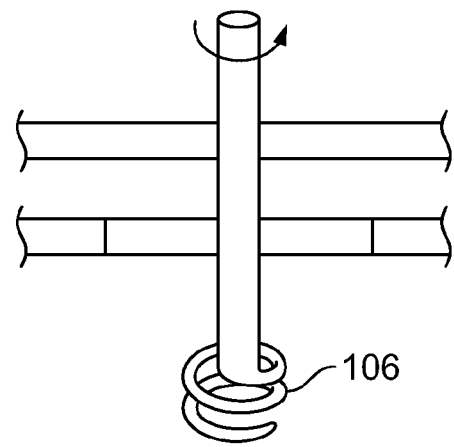
Figure 6C:
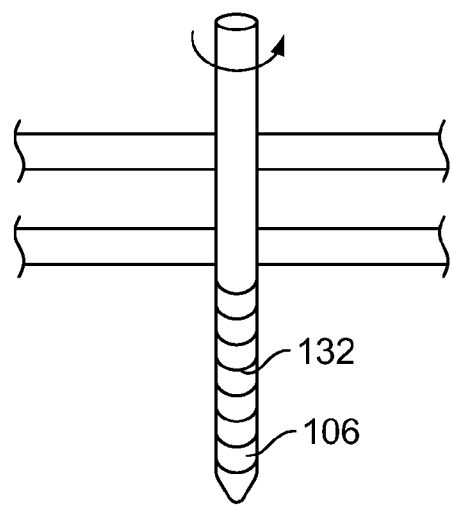

FIGS. 6A-6C illustrate additional variations of electrodes 106 for use within the current devices. In these cases, the electrode 106 rotates as it penetrates tissue. FIG. 6A shows a rotating blade-type configuration where part or all of the blade may have an exposed conductive surface for establishing a current path. Alternatively, a single blade may have both the poles of the circuit such that the electrode pair is on a single electrode.

FIG. 6B illustrates a cork-screw or helical type electrode. FIG. 6C shows an electrode 106 having a threaded portion 132.

Figure 7A:
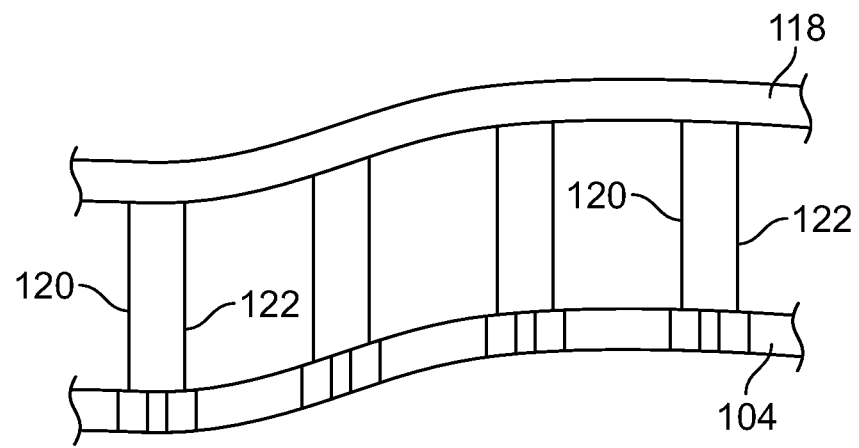
FIGS. 7A to 7B show additional modes of contouring the treatment unit to varying skin geometries.

Variations of the present device may include treatment units having features to allow for treatment of contoured surfaces. For example, FIG. 7A illustrates a contoured faceplate 104. The contour of the faceplate 104 may be selected depending on the intended area of treatment. For example, a medical practitioner may have a range of contoured surfaces and could choose one depending on the shape of patient's face. In the illustrated variation, the electrode plate 118 may also be contoured (e.g., to match the faceplate or otherwise). As shown, the electrodes 120, 122 can be sized such that a uniform length extends beyond the faceplate. However, variations also include electrodes having varying lengths that extend from the faceplate.

Figure 7B:
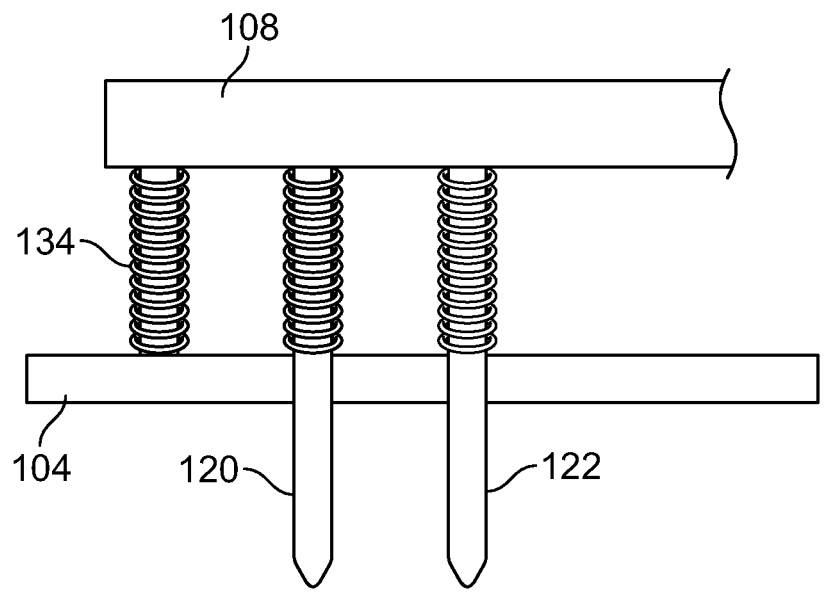

FIG. 7B illustrates a variation having a double spring configuration. The first spring 134 is placed between the faceplate 104 and the electrode plate 118. One or more additional springs are placed on the electrodes 120, 122. Again, such a configuration assists in placing the faceplate 104 against tissue as well as adjusting for contours in the skin surface.

Figure 8A:
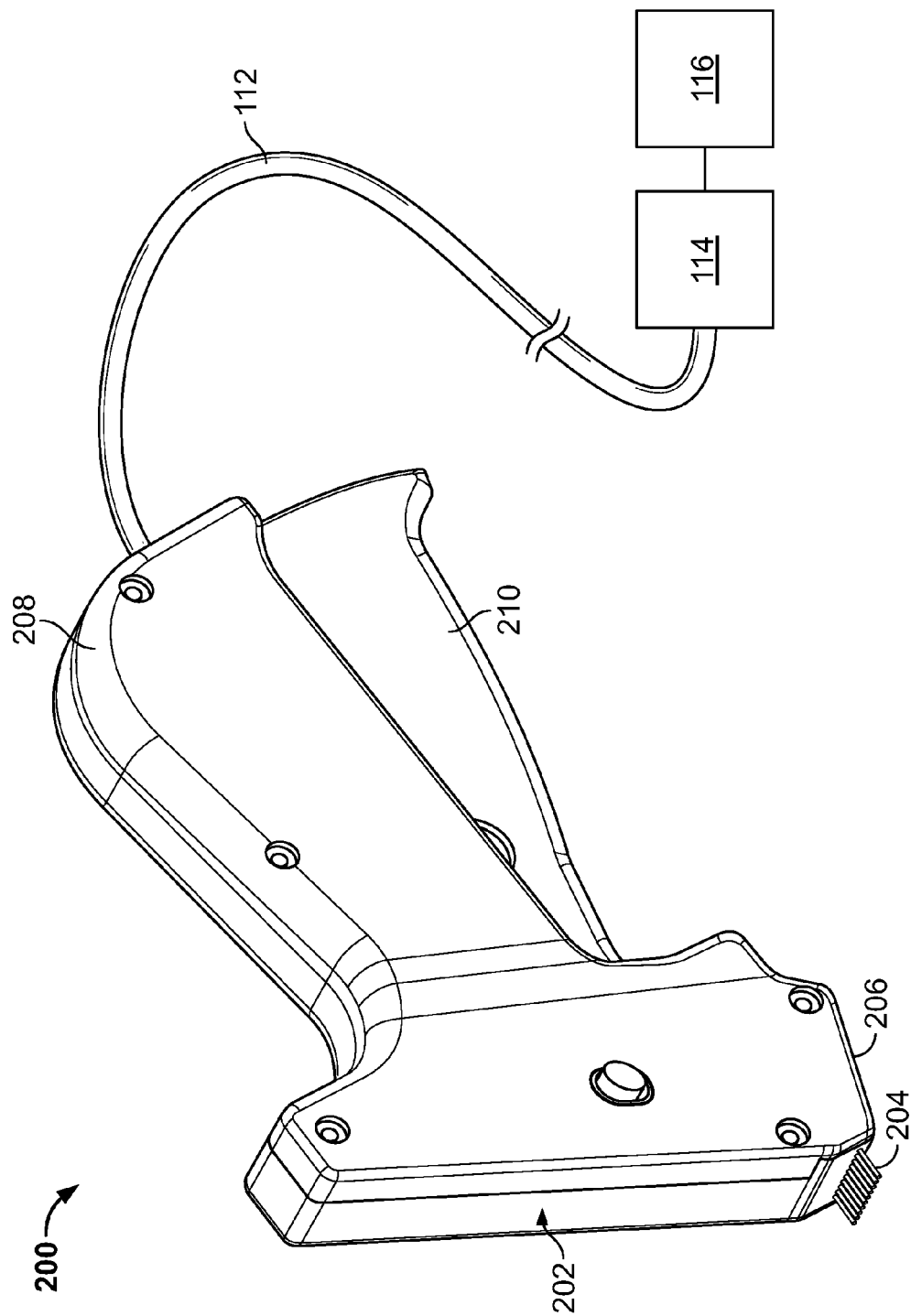
FIG. 8A shows an additional variation of a device having an array of electrodes adjacent to a tissue engaging surface.

FIG. 8A illustrates another variation of a treatment unit 200 for use in accordance with the principles discussed herein. In this variation, the unit 200 includes a body portion 202 from which a cannula or introducer member 204 extend at an oblique angle relative to a tissue engagement surface 206. As described below, the ability to insert the electrodes (not shown) into the tissue at an oblique angle increases the treatment area and allows for improved cooling at the tissue surface. Although the variation only shows a single array of introducers for electrodes, variations of the invention may include multiple arrays of electrodes. In addition, the devices and systems described below may be combined with the features described herein to allow for improved penetration of tissue. The devices of the present invention may have an angle A of 15 degrees. However, the angle may be anywhere from ranging between 5 and 85 degrees.

Although the introducer member 204 is shown as being stationary, variations of the device include introducer members that are slidable on the electrodes. For example, to ease insertion of the electrode, the electrode may be advanced into the tissue. After the electrode is in the tissue, the introducer member slides over the electrode to a desired location. Typically, the introducer member is insulated and effectively determines the active region of the electrode. In another variation using RF energy, the introducer member may have a return electrode on its tip. Accordingly, after it advances into the tissue, application of energy creates current path between the electrode and the return electrode on the introducer.

The body 202 of the electrode device 200 may also include a handle portion 208 that allows the user to manipulate the device 200. In this variation, the handle portion 208 includes a lever or lever means 210 that actuates the electrodes into the tissue (as discussed in further detail below).

As discussed above, the electrode device 200 can be coupled to a power supply 114 with or without an auxiliary unit 116 via a connector or coupling member 112. In some variations of the device, a display or user interface can be located on the body of the device 200 as discussed below.

Figure 8B:
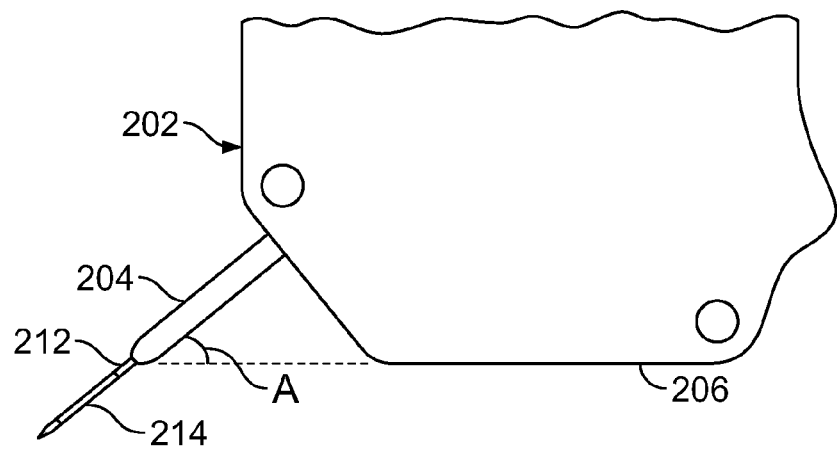
FIG. 8B shows a magnified view of the electrodes and tissue engaging surface of the device of FIG. 8A.

FIG. 8B illustrates a partial side view of the electrodes 212 and tissue engaging surface 206 of the electrode device of FIG. 8A. As shown, the electrodes 212 extend from the device 200 through the cannula 204. In alternate variations, the electrodes can extend directly from the body of the device or through extensions on the device.

As shown, the electrodes 212 are advanceable from the body 202 (in this case through the introducers 204) in an oblique angle A as measured relative to the tissue engagement surface 206. The tissue engagement surface 206 allows a user to place the device on the surface of tissue and advance the electrodes 212 to the desired depth of tissue. Because the tissue engagement surface 206 provides a consistent starting point for the electrodes, as the electrodes 212 advance from the device 202 they are driven to a uniform depth in the tissue.

For instance, without a tissue engagement surface, the electrode 212 may be advanced too far or may not be advanced far enough such that they would partially extend out of the skin. As discussed above, either case presents undesirable outcomes when attempting to treat the dermis layer for cosmetic affects. In cases where the device is used for tumor ablation, inaccurate placement may result in insufficient treatment of the target area.

Figure 8C:
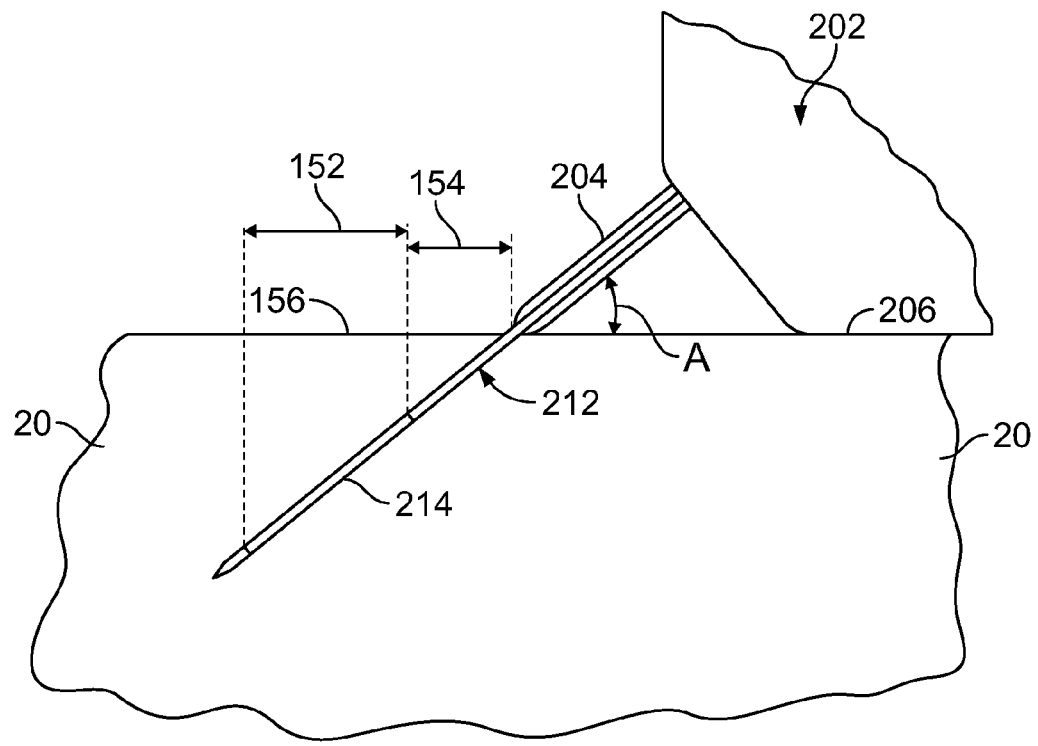
FIGS. 8C to 8D show an example of an electrode entering tissue at an oblique angle adjacent to a tissue engaging surface.

FIG. 8C illustrates a magnified view of the electrode entering tissue 20 at an oblique angle A with the tissue engaging surface 206 resting on the surface of the tissue 20. As is shown, the electrode 212 can include an active area 214. Generally, the term "active area" refers to the part of the electrode through which energy is transferred to or from the tissue. For example, the active area could be a conductive portion of an electrode, it can be a resistively heated portion of the electrode, or even comprise a window through which energy transmits to the tissue. Although this variation shows the active area 214 as extending over a portion of the electrode, variations of the device include electrodes 212 having larger or smaller active areas 214.

In any case, because the electrodes 212 enter the tissue at an angle A, the resulting region of treatment 152, corresponding to the active area 214 of the electrode is larger than if the needle were driven perpendicular to the tissue surface. This configuration permits a larger treatment area with fewer electrodes 212. In addition, the margin for error of locating the active region 214 in the desired tissue region is greater since the length of the desired tissue region is greater at angle A than if the electrode were deployed perpendicularly to the tissue.

As noted herein, the electrodes 212 may be inserted into the tissue in either a single motion where penetration of the tissue and advancement into the tissue are part of the same movement or act. However, variations include the use of a spring mechanism or impact mechanism to drive the electrodes 212 into the tissue. Driving the electrodes 212 with such a spring-force increases the momentum of the electrodes as they approach tissue and facilitates improved penetration into the tissue. As shown below, variations of the devices discussed herein may be fabricated to provide for a dual action to insert the electrodes. For example, the first action may comprise use of a spring or impact mechanism to initially drive the electrodes to simply penetrate the tissue. Use of the spring force or impact mechanism to drive the electrodes may overcome the initial resistance in puncturing the tissue. The next action would then be an advancement of the electrodes so that they reach their intended target site. The impact mechanism may be spring driven, fluid driven or via other means known by those skilled in the art. One possible configuration is to use an impact or spring mechanism to fully drive the electrodes to their intended depth.

Figure 8D:
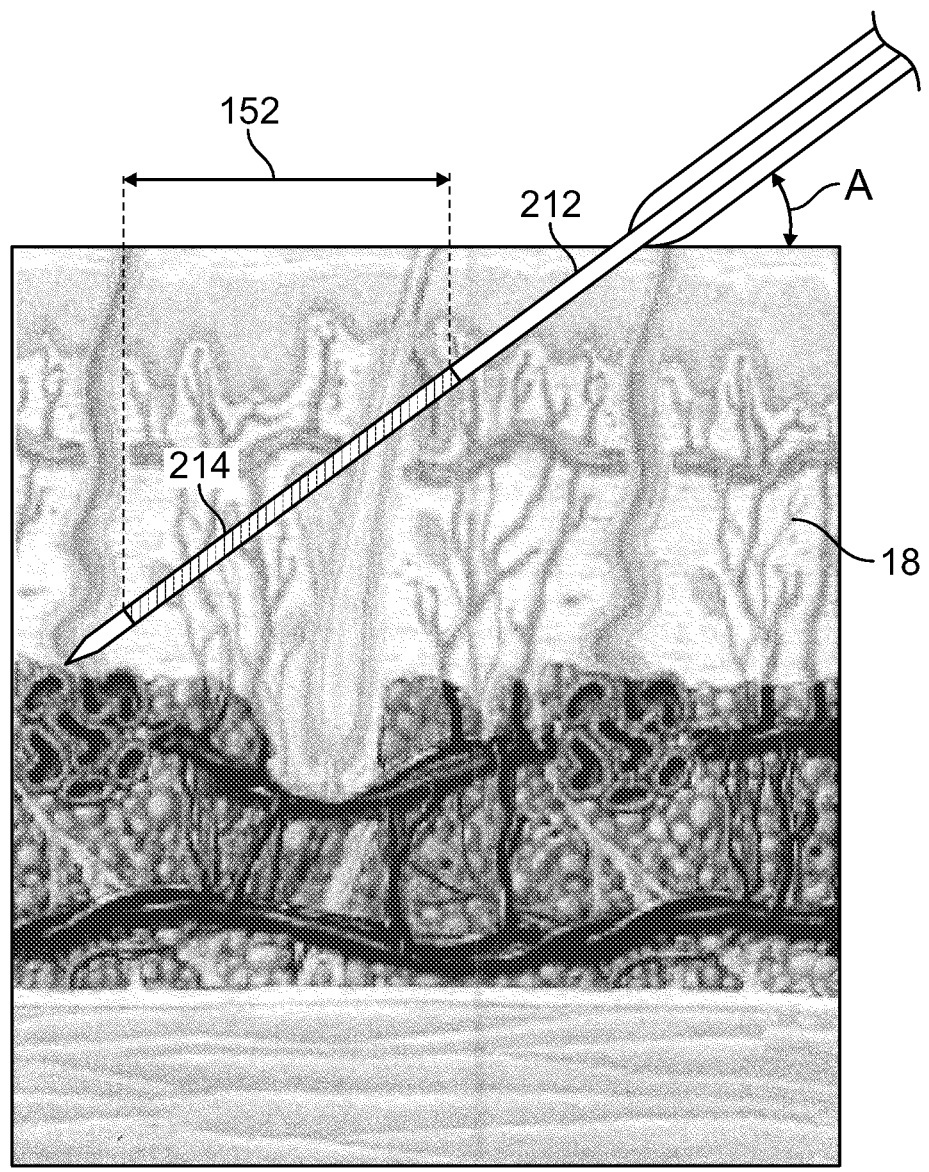

FIG. 8D illustrates an example of the benefit of oblique entry when the device is used to treat the dermis 18. As shown, the length of the dermis 18 along the active region 214 is greater than a depth of the dermis 18. Accordingly, when trying to insert the electrode in a perpendicular manner, the shorter depth provides less of a margin for error when trying to selectively treat the dermis region 18.

Inserting the electrode at angle A also allows for direct cooling of the surface tissue. As shown in FIG. 8C, the area of tissue on the surface 156 that is directly adjacent or above the treated region 152 (i.e., the region treated by the active area 214 of the electrode 212) is spaced from the entry point by a distance or gap 154. This gap 154 allows for direct cooling of the entire surface 156 adjacent to the treated region 152 without interference by the electrode or the electrode mounting structure. In contrast, if the electrode were driven perpendicularly to the tissue surface, then cooling must occur at or around the perpendicular entry point.

Figure 8E:
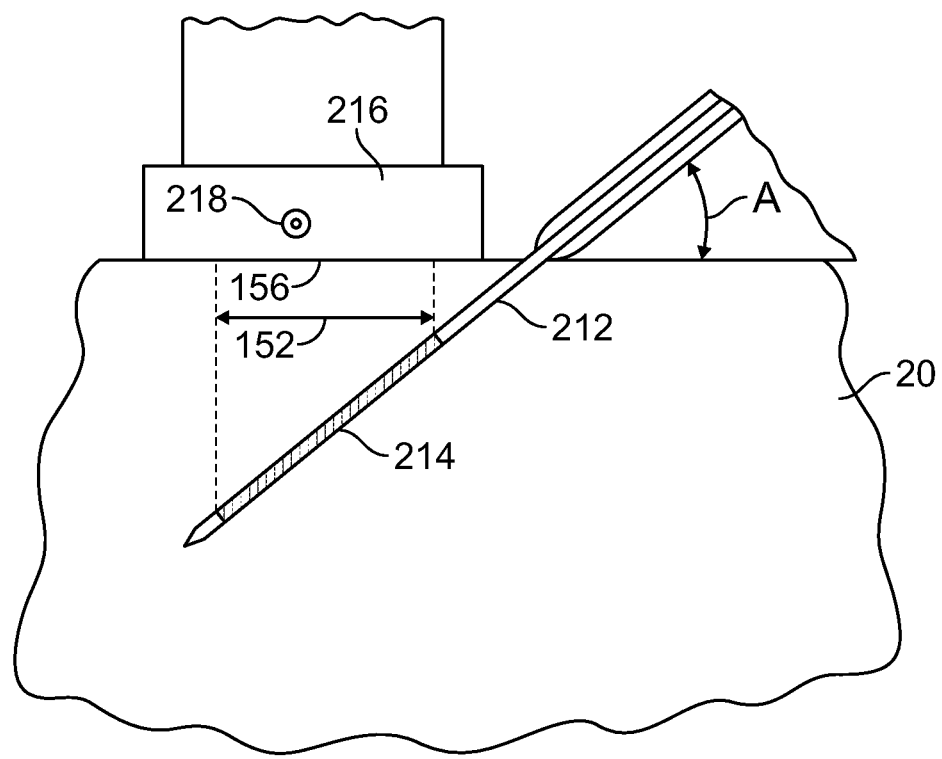
FIG. 8E to 8F show cooling surfaces adjacent to the electrodes.

FIG. 8E illustrates one example of a cooling surface 216 placed on body structure or tissue 20. As shown, the electrode 212 enters at an oblique angle A such that the active region 214 of the electrode 212 is directly adjacent or below the cooling surface 216. In certain variations, the cooling surface may extend to the entry point (or beyond) of the electrode 212. However, it is desirable to have the cooling surface 216 over the electrode's active region 214 because the heat generated by the active region 212 will be greatest at the surface 156. In some variations, devices and methods described herein may also incorporate a cooling source in the tissue engagement surface.

The cooling surface 216 may be any cooling mechanism known by those skilled in the art. For example, it may be a manifold type block having liquid or gas flowing through for convective cooling. Alternatively, the cooling surface 216 may be cooled by a thermoelectric cooling device (such as a fan or a Peltier-type cooling device). In such a case, the cooling may be driven by energy from the electrode device thus eliminating the need for additional fluid supplies. One variation of a device includes a cooling surface 216 having a temperature detector 218 (thermocouple, RTD, optical measurement, or other such temperature measurement device) placed within the cooling surface. The device may have one or more temperature detectors 218 placed anywhere throughout the cooling surface 216 or even at the surface that contacts the tissue.

In one application, the cooling surface 216 is maintained at or near body temperature. Accordingly, as the energy transfer occurs causing the temperature of the surface 156 to increase, contact between the cooling surface 216 and the tissue 20 shall cause the cooling surface to increase in temperature as the interface reaches a temperature equilibrium. Accordingly, as the device's control system senses an increase in temperature of the cooling surface 216 additional cooling can be applied thereto via increased fluid flow or increased energy supplied to the Peltier device.

While the cooling surface may comprise any commonly known thermally conductive material, metal, or compound (e.g., copper, steel, aluminum, etc.). Variations of the devices described herein may incorporate a translucent or even transparent cooling surface. In such cases, the cooling device will be situated so that it does not obscure a view of the surface tissue above the region of treatment.

In one variation, the cooling surface can include a single crystal aluminum oxide ($Al_2O_3$). The benefit of the single crystal aluminum oxide is a high thermal conductivity optical clarity, ability to withstand a large temperature range, and the ability to fabricate the single crystal aluminum oxide into various shapes. A number of other optically transparent or translucent substances could be used as well (e.g., diamond, other crystals or glass).

Figure 8F:
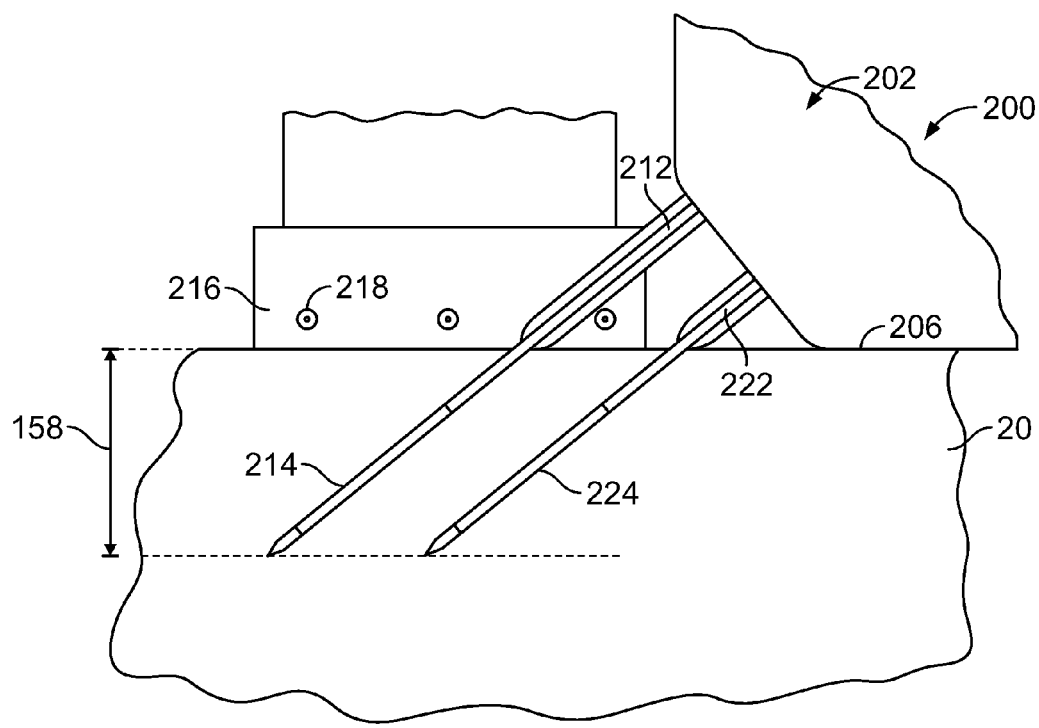

FIG. 8F illustrates another aspect for use with variations of the devices and methods described herein. In this variation, the device 200 includes two arrays of electrodes 212, 222. As shown, the first plurality 212 is spaced evenly apart from and parallel to the second plurality 222 of electrodes. In addition, as shown, the first set of electrodes 212 has a first length while the second set of electrodes 222 has a second length, where the length of each electrode is chosen such that the sets of electrodes 212, 222 extend into the tissue 20 by the same vertical distance or length 158. Although only two arrays of electrodes are shown, variations of the invention include any number of arrays as required by the particular application. In some variations, the lengths of the electrodes 212, 222 are the same. However, the electrodes will be inserted or advanced by different amounts so that their active regions penetrate a uniform amount into the tissue. As shown, the cooling surface may include more than one temperature detecting element 218.

FIG. 8F also illustrates a cooling surface 216 located above the active regions 214, 224 of the electrodes. In such a variation, it may be necessary for one or more of the electrode arrays to pass through a portion of the cooling surface 216. Alternative variations of the device include electrodes that pass through a portion of the cooling device (such as the Peltier device described below).

Figure 8G:
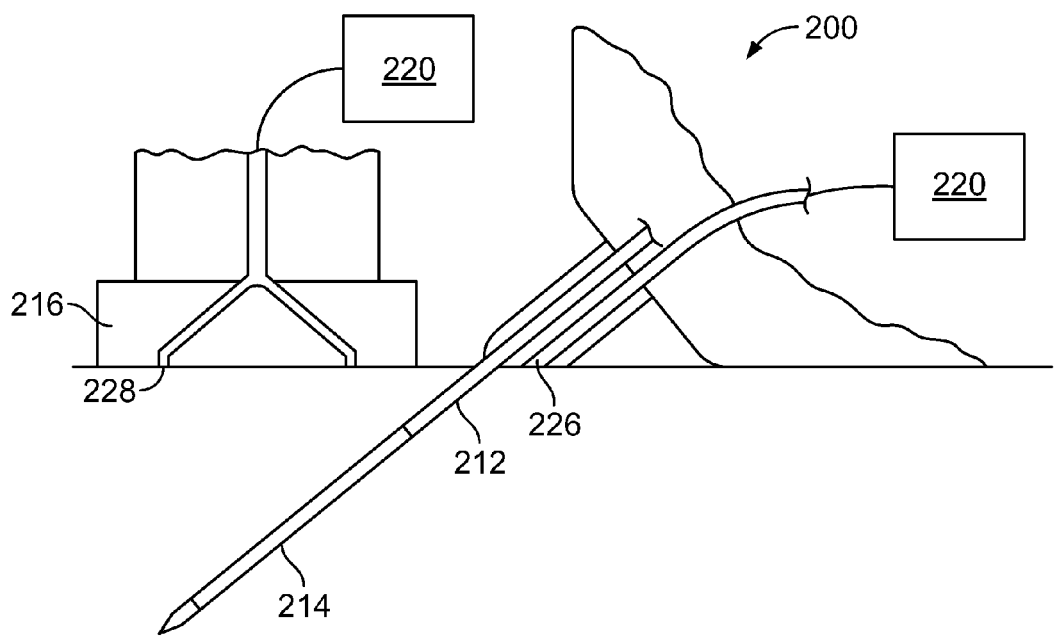
FIG. 8G shows a variation of a device having a marking assembly.

FIG. 8G shows an aspect for use with methods and devices of the invention that allows marking of the treatment site. As shown, the device 200 may include one or more marking lumens 226, 228 that are coupled to a marking ink 220. During use, a medical practitioner may be unable to see areas once treated. The use of marking allows the practitioner to place a mark at the treatment location to avoid excessive treatments. As shown, a marking lumen 226 may be placed proximate to the electrode 212. Alternatively, or in combination, marking may occur at or near the cooling surface 216 since the cooling surface is directly above the treated region of tissue. The marking lumens may be combined with or replaced by marking pads. Furthermore, any type of medically approved dye may be used to mark. Alternatively, the dye may comprise a substance that is visible under certain wavelengths of light. Naturally, such a feature permits marking and visualization by the practitioner given illumination by the proper light source but prevents the patient from seeing the dye subsequent to the treatment.

Figure 9A:
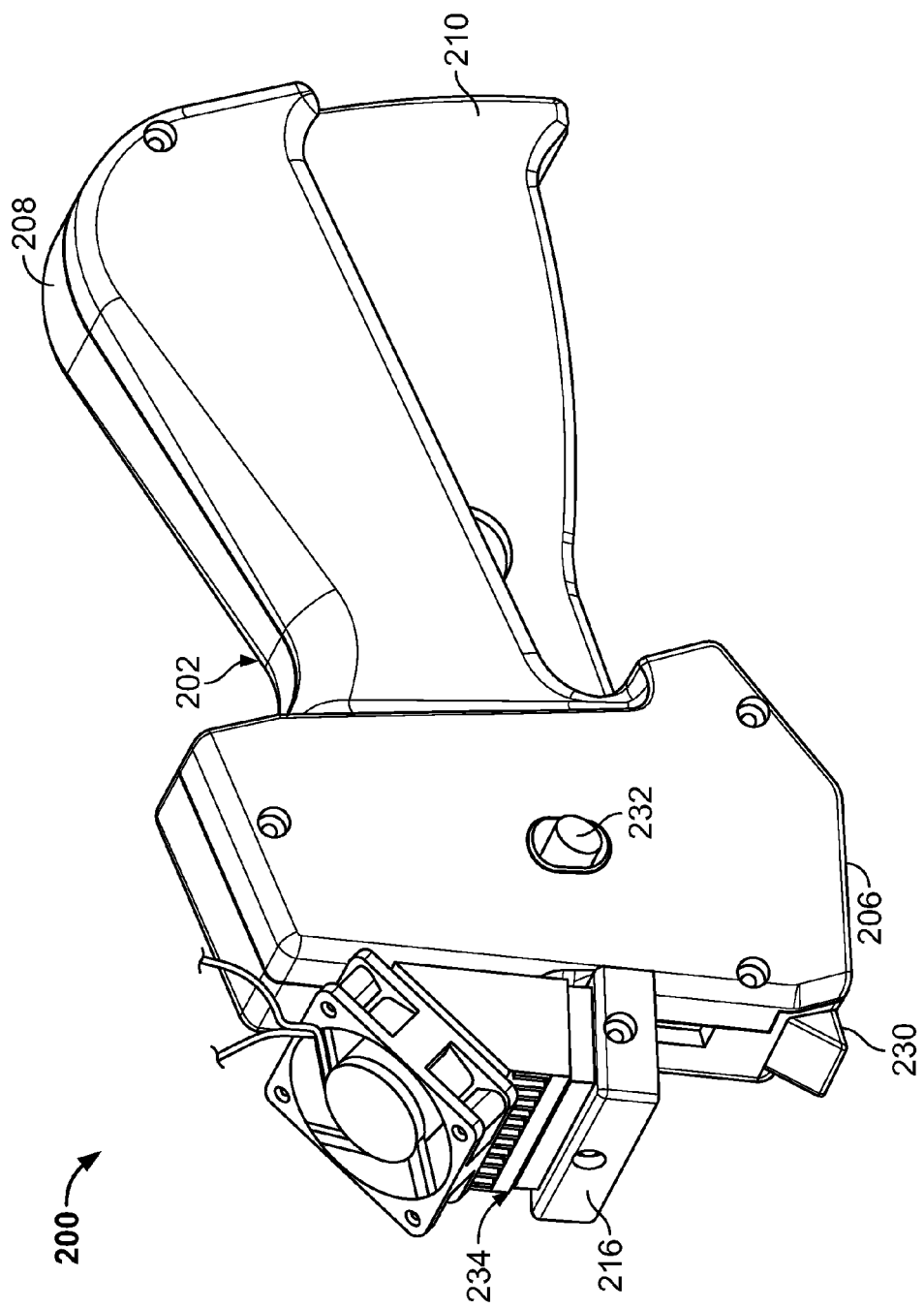

FIG. 9A illustrates a variation of a device 200 that may incorporate the aspects described herein. As shown, the device 200 includes a body portion 202 having a handle 208 and an actuating trigger or lever 210. The device 200 couples power supply and other necessary auxiliary components though they are not illustrated. In this variation, the electrodes may be placed behind an electrode covering 230. The covering 230 may be purely cosmetic or may function as the introducers discussed above. In the illustrated variation, the cooling surface 216 is coupled to a Peltier cooling device 234. Although the cooling surface 216 is shown as being retracted from the tissue engagement surface 206, the cooling surface may be lowered when necessary to maintain the surface tissue during treatment. As noted above, variations of the device may include an impact means to drive the electrodes into tissue. In this variation, the device 200 includes a reset knob 232 so that the practitioner may re-engage the impact mechanism or spring mechanism between treatments. Alternatively, the reset-knob may be configured to withdraw the electrodes from the tissue and into the device after treatment.

FIG. 9B illustrates a cross-sectional side view of the device 200 of FIG. 9A. As shown, the lever 210 is coupled to an electrode base or electrode plate 228 to drive the electrodes 212 into tissue. In this variation, the actuating assembly also includes an impact mechanism 236 that, at least, initially drives the electrodes 212 into tissue to overcome the resistance when penetrating the surface of tissue.

Figure 9C:
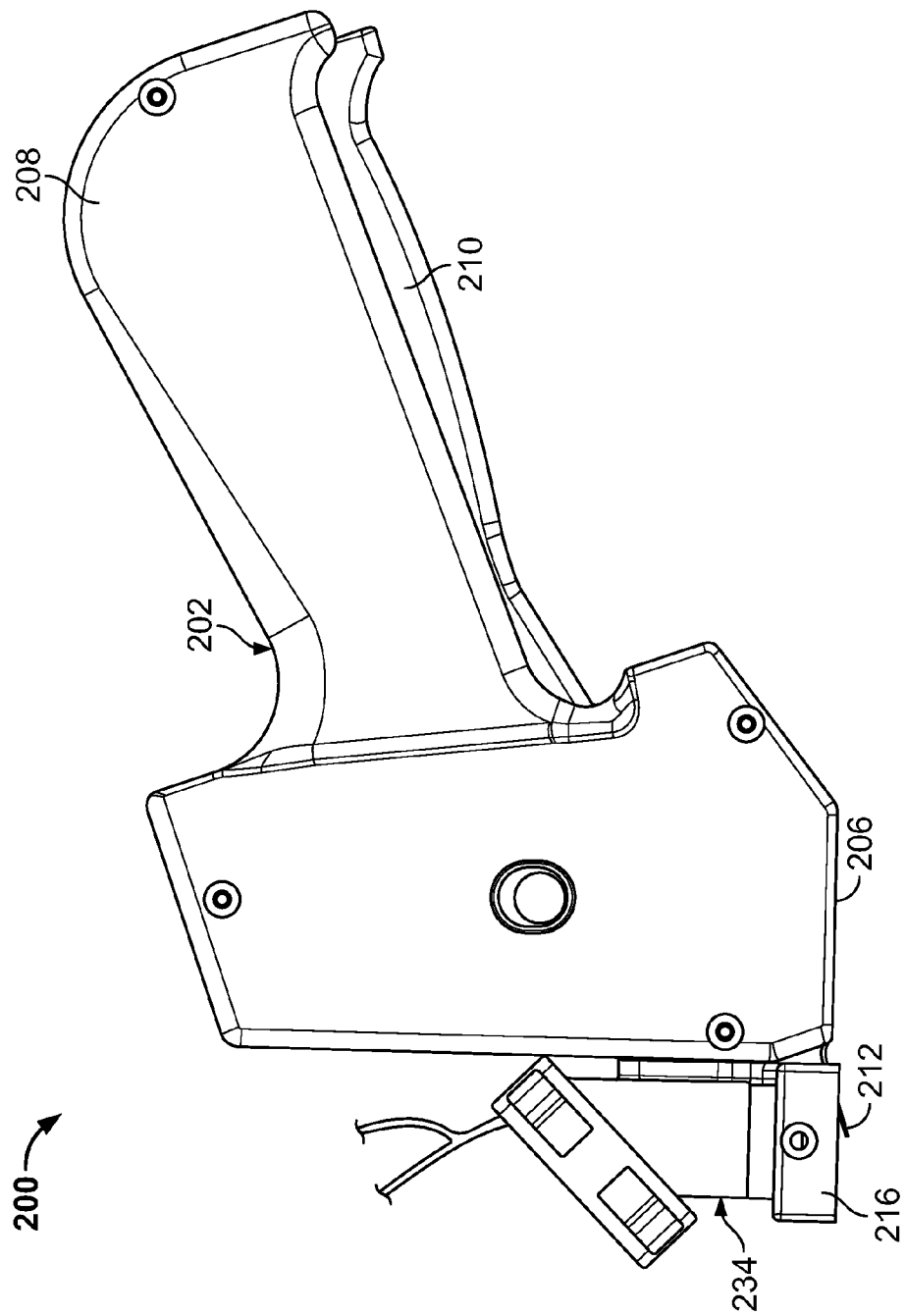

FIG. 9C illustrates a side view of the device 200 of FIG. 9A when the cooling surface 216 is parallel to the tissue engaging surface 206 and directly above the electrodes 212 when advanced from the device body 202. In this variation, the electrodes 212 at least partially extend through the cooling surface 216. However, the cooling surface 216 is still able to make direct contact with a surface of tissue directly above the active area of the electrodes.

FIG. 9C also shows a Peltier cooling device 234 coupled to the cooling surface 216. As noted herein, any number of cooling sources may be used. However, in this variation, the Peltier cooling device 234 eliminates the need for a fluid source. In some cases, the cooling device 234 can be powered using the same power supply that energizes the electrodes 212. Such a configuration provides a more compact design that is easier for a medical practitioner to manipulate.

Figure 9D:
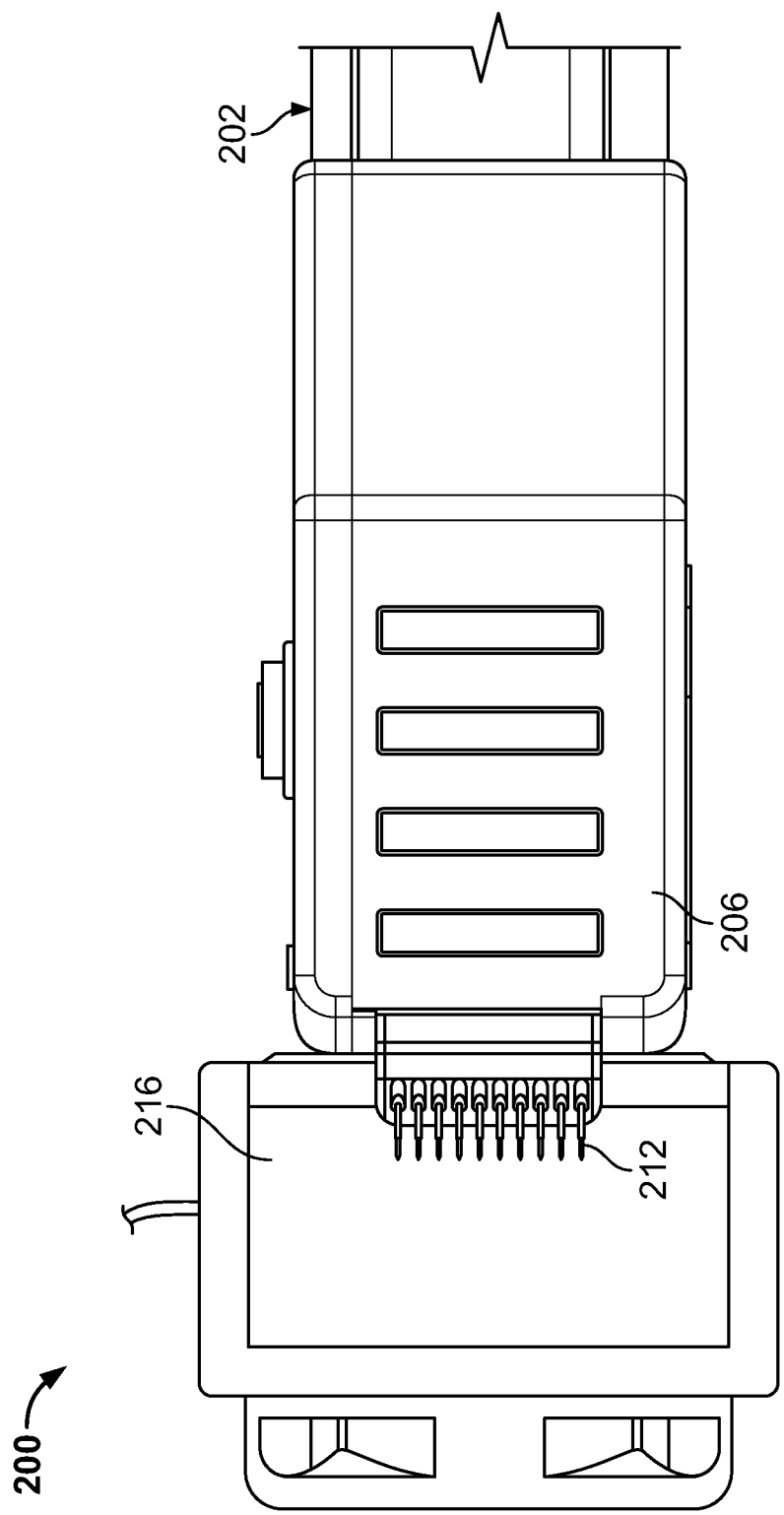

FIG. 9D illustrates a bottom view of the device 200 of FIG. 9C. As shown the electrodes 212 directly below the cooling surface 216 when extended from the body of the device 202.

Figure 10A:
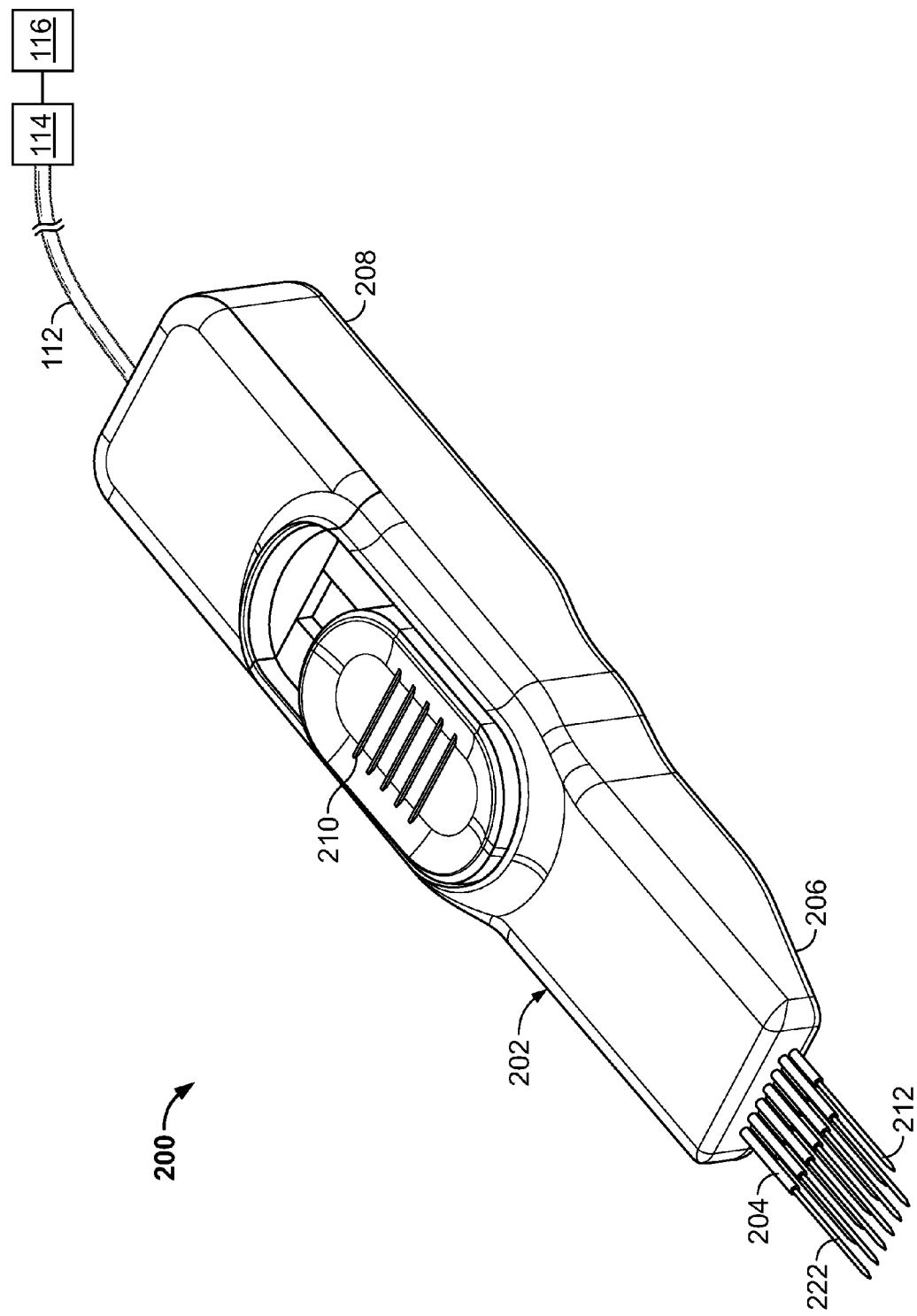
FIGS. 10A to 10B show an additional variation of an electrode device.

FIG. 10A illustrates another variation of an electrode device 200. In this variation, the lever 210 or actuator is on the top of the handle portion 208. The lever 210 may be manually operated in that the medical practitioner advances the lever 210 to advance the electrodes 212 into tissue. Alternatively, or in combination a spring mechanism or even a source of compressed gas (stored in the body 202 or coupled via a connector 112) may be used to drive the electrodes 212 from the introducers 204 and into the tissue.

Figure 10B:
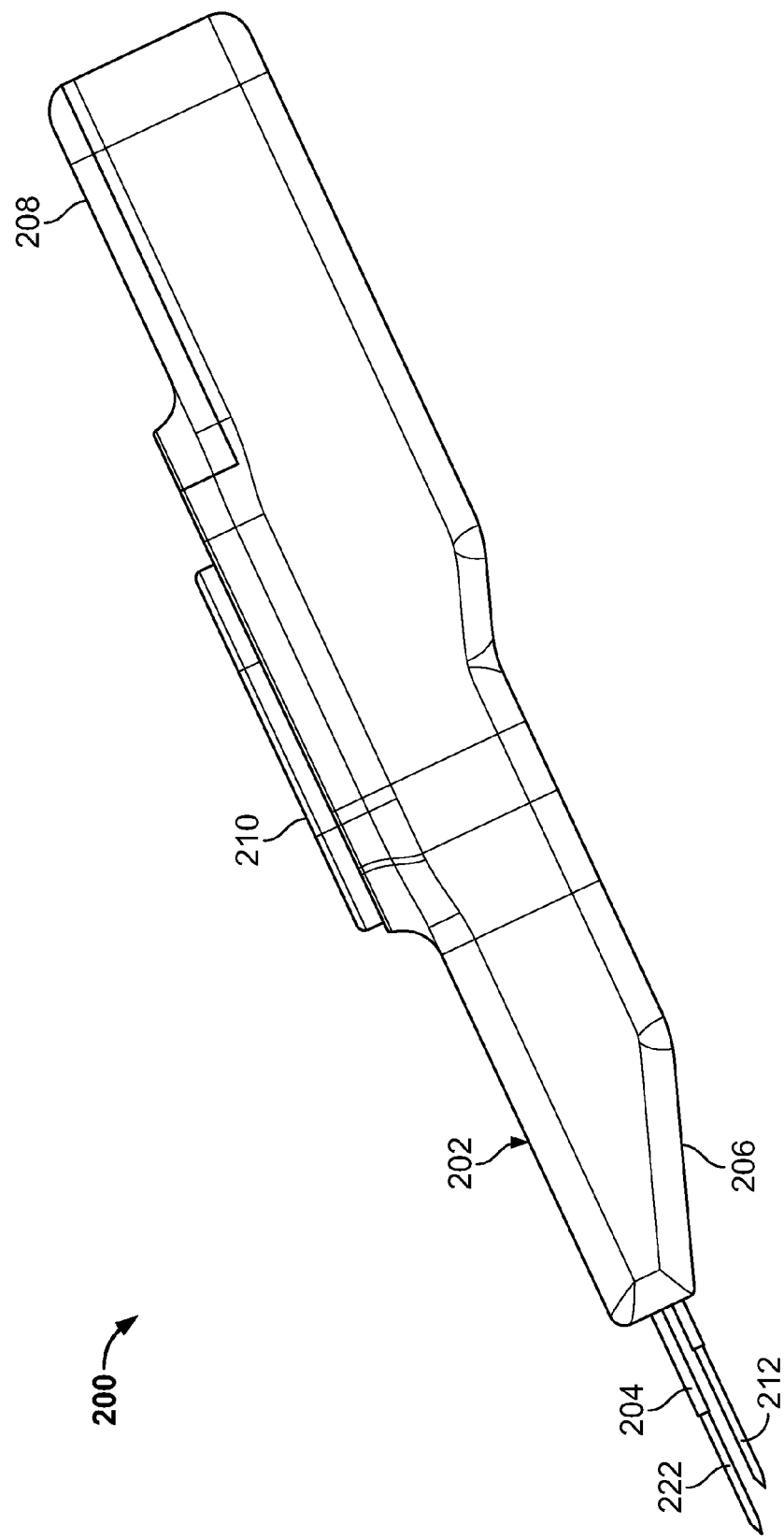

FIG. 10B illustrates a side view of the device 200 of FIG. 10A. As shown, the tissue engaging surface 206 is parallel to the ends of the introducers 204. Accordingly, to deliver the electrodes 212, 222 to a uniform depth, the lengths of the electrodes 212, 222 may vary accordingly.

Figure 11:
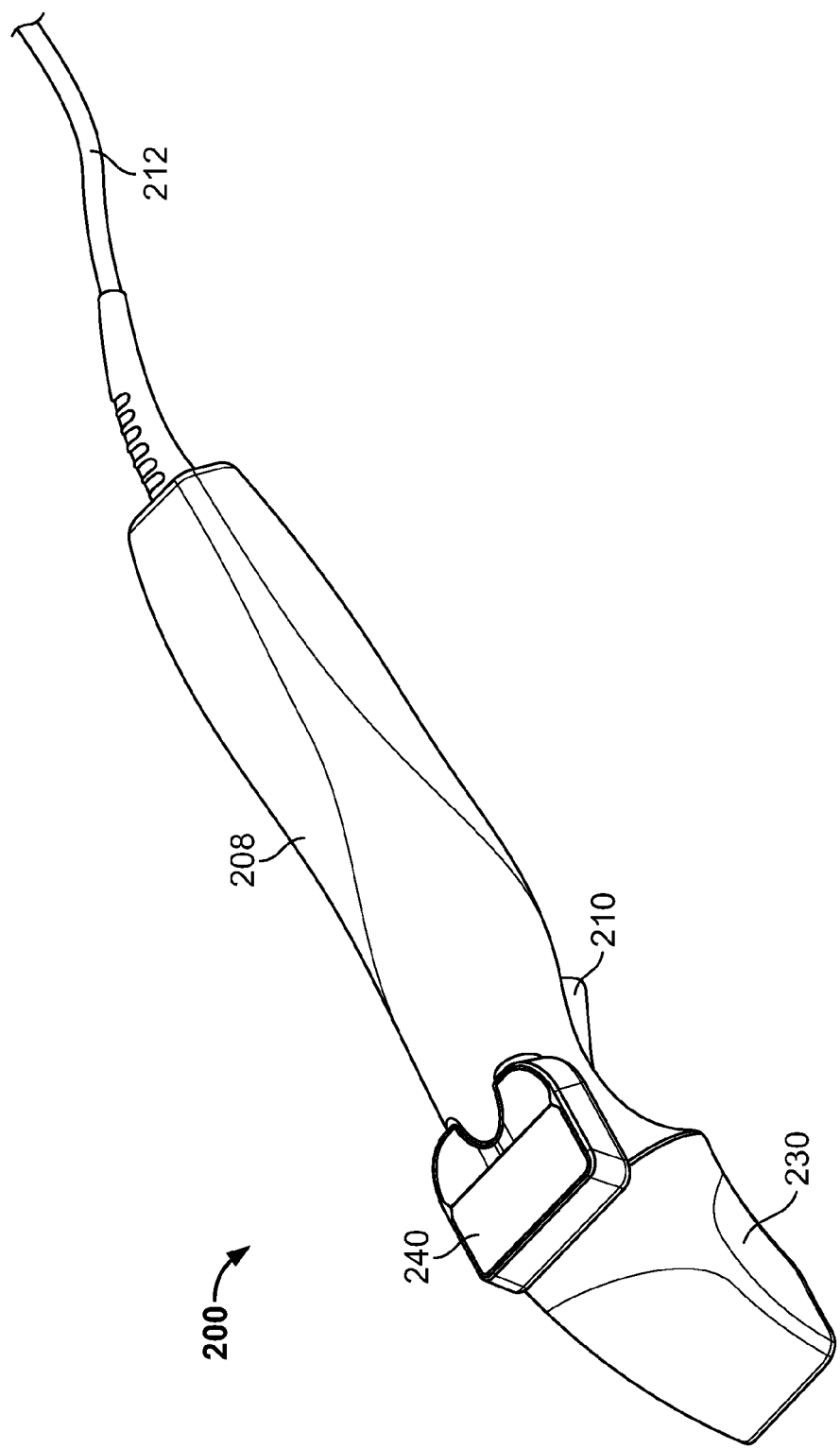
FIG. 11 shows a variation of an electrode device having a user interface on a body portion.

FIG. 11 shows a variation of a device 200 having additional aspects for combination with the methods and devices described herein. As shown, the device 200 may include an electrode covering 230 to shield the electrodes from damage or view. In the latter case, hiding the electrodes from view may be desirable for additional patient comfort. FIG. 11 also illustrates a user interface 240. The user interface 240 may display such information as whether the system is ready for treatment, the temperature of the cooling surface, the duration of the particular treatment, the number of treatments or any other information regarding the procedure or patient.

The variations in FIGS. 10A-11 are shown without a cooling surface. However, incorporating cooling surfaces with the respective device bodies is within the scope of this disclosure.

Figure 12A:
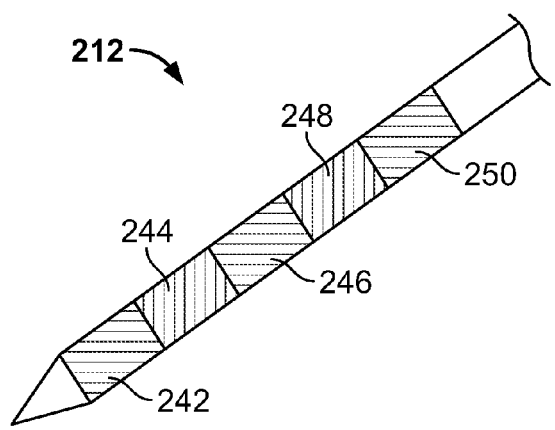
FIGS. 12A-12D illustrate variations of electrodes having varying resistance or impedance along the length of the electrode.
Figure 12B:
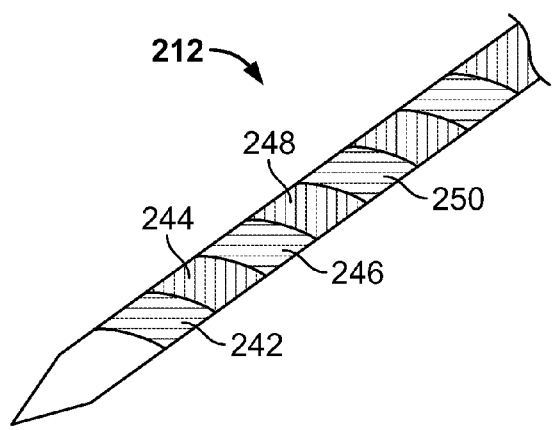
Figure 12C:
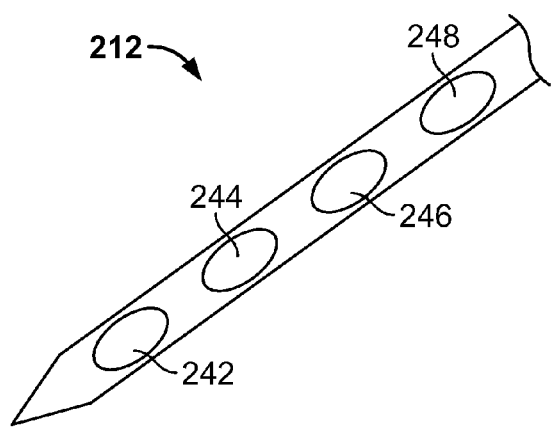
Figure 12D:
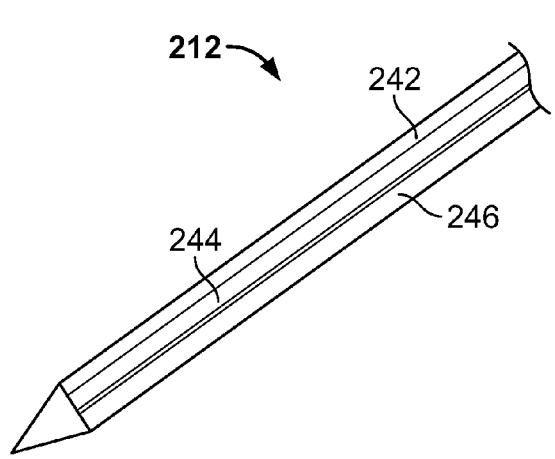

FIGS. 12A-12D illustrate variations of electrodes for use with the systems and methods described herein. Depending upon the application, it may be desirable to provide an electrode 212 that has a variable resistance along the active region of the electrode 212. FIGS. 12A-12D illustrate a partial example of such electrodes. As shown in FIGS. 12A and 12B, an electrode may have concentric or spiral bands that create varying ranges of impedance 242, 244, 246, 248, and 250 along the electrode 212. In addition, as shown in FIG. 12C, the electrode 212 may have regions 242, 244, 246, and 248 along the electrode of varying resistance. FIG. 12D illustrates a similar concept where the regions of resistance 242, 244, 246 run in longitudinal stripes along the electrode 212. These configurations may be fabricated through spraying, dipping, plating, anodizing, plasma treating, electro-discharge, chemical applications, etching, etc.

Figure 13A:
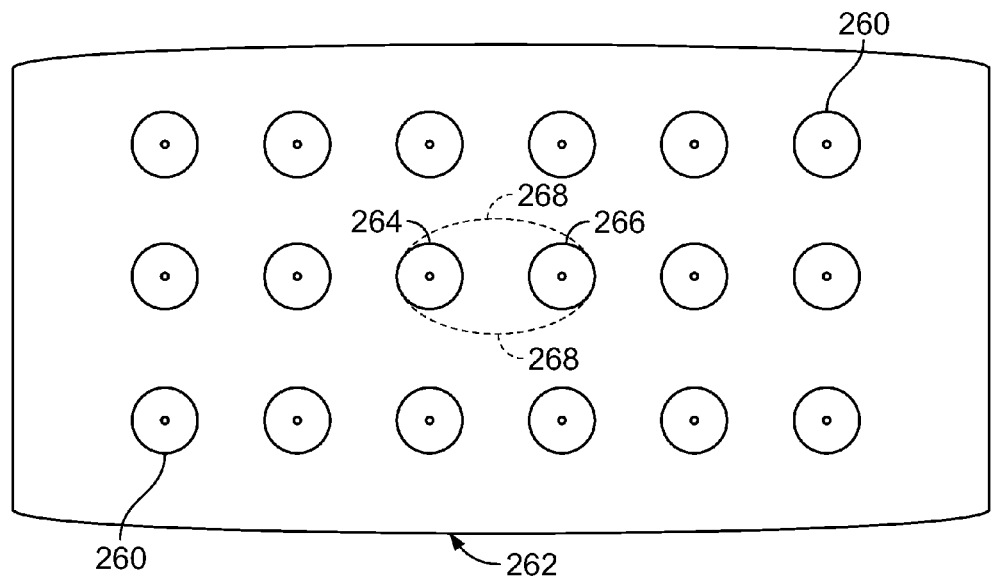
FIGS. 13A to 13B show an example of an array of electrodes where any number of pairs of electrodes can be triggered to apply therapeutic energy to tissue.
Figure 13B:
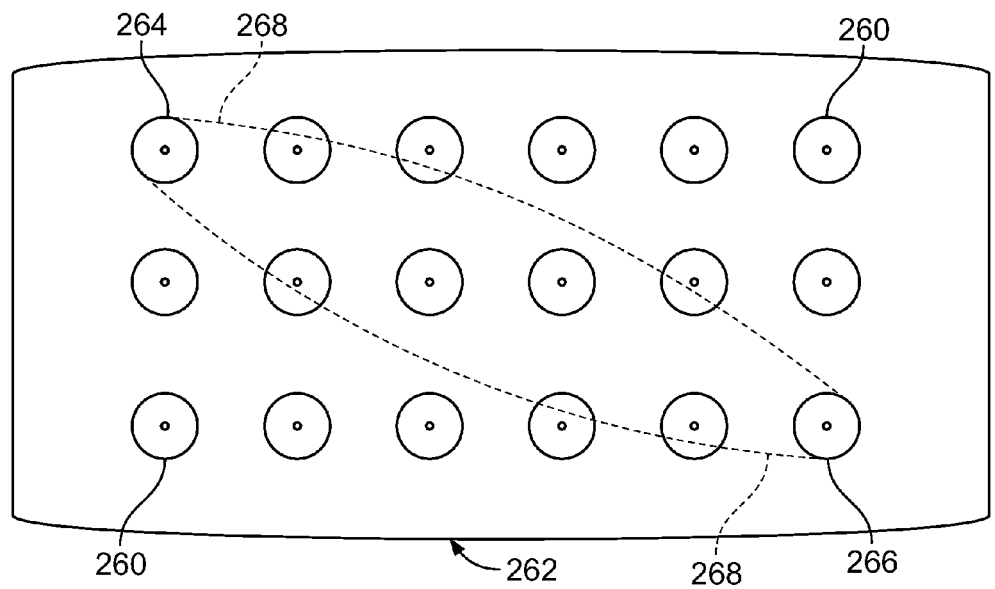

FIGS. 13A-13B illustrate examples of system configurations that can be incorporated into any conventional electrode array or into the devices described above using RF energy. As shown, in this example the electrode array 262 comprises a 3×6 array of electrode. Each electrode in the array 262 is configured to energize separately. This configuration provides the ability of any given pair of electrodes to form a circuit for treating tissue. In one example, in the variation of FIG. 13A, the power supply energizes adjacent electrode pairs 264, 266. This configuration generates the smallest treatment area in the electrode array 262. FIG. 13B illustrates a situation where the farthest electrode pairs 264, 266 within the array 262 are triggered to form a current path 268. One benefit of this configuration is that a single electrode array may form a number of patterns based on various combinations of pairs that may be formed in the array. The array may be able to provide a denser treatment or more uniform tissue heating. The treatment can deliver targeted therapy to key areas of tissue. In one variation, the electrode array may trigger various pairs sequentially during a single insertion.

Although the systems described herein may be used by themselves, the invention includes the methods and devices described above in combination with moisturizer, ointments, etc. that increase the resistivity of the epidermis. Accordingly, prior to the treatment, the medical practitioner can prepare the patient by increasing the resistivity of the epidermis. During the treatment, because of the increased resistivity of the epidermis, energy would tend to flow in the dermis.

The above variations are intended to demonstrate the various examples of embodiments of the methods and devices of the invention. It is understood that the embodiments described above may be combined or the aspects of the embodiments may be combined in the claims.

What is claimed is:

1. An electrode device for treating a target region beneath a surface of tissue, the device comprising:
   a device body having a handle portion, and a tissue engaging surface, where the tissue engaging surface allows orientation of the device body on the surface of tissue;
   a first plurality of electrodes being configured to enter the surface of tissue at an oblique angle relative to the tissue engaging surface for positioning in the target region of tissue when the tissue engaging surface is placed on the surface of tissue;
   where each electrode includes an active region located at a distal portion thereof;
   a connector adapted to couple an energy supply to the plurality of electrodes; and
   a cooling surface separated from the plurality of electrodes along the surface of tissue such that the cooling surface is adapted to engage an area of the tissue surface directly above the active region of the electrodes when the electrodes are advanced from the device body, and where the cooling surface is adapted to cool the surface of tissue upon the application of energy to the electrode.

2. The electrode device of claim 1, where the cooling surface cools the surface of tissue by maintaining a temperature at, below, or slightly above body temperature.

3. The electrode device of claim 2, where the cooling surface is visually transparent.

4. The electrode device of claim 2, where the cooling surface is visually translucent.

5. The electrode device of claim 4, where the cooling surface comprises a silica based glass.

6. The electrode device of claim 4, where the cooling surface comprises a single crystal aluminum oxide material.

7. The electrode device of claim 2, where the cooling surface comprises a material selected from the group consisting of steel, aluminum, and copper.

8. The electrode device of claim 2, where the plurality of electrodes pass through a portion of the cooling surface when advanced from the device body.

9. The electrode device of claim 2, further comprising a fluid source coupled to the cooling surface, where the fluid source is adapted to maintain the temperature.

10. The electrode device of claim 2, further comprising a thermoelectric cooling device coupled to the power supply and in contact with the cooling surface, where the thermoelectric cooling device maintains the temperature.

11. The electrode device of claim 10, where the thermoelectric cooling device comprises a Peltier cooling device.

12. The electrode device of claim 1, where the device further comprises a second plurality of electrodes each spaced apart and parallel to the first plurality of electrodes, where the second plurality of electrodes includes the active region.

13. The electrode device of claim 12, where the first and second plurality of electrodes comprise a first length, and the second plurality of electrodes comprise a second length, where the first and second length not equal such that upon insertion into tissue, each plurality of needles extends a same vertical length into the tissue.

14. The electrode device of claim 1, where the first plurality of electrodes are axially moveable along the oblique angle.

15. The electrode device of claim 1, where the plurality of electrodes extends from a plurality of cannulae extending from the device body at the oblique angle.

16. The electrode device of claim 1, where each of the plurality of electrodes has a respective impedance along the respective active region, and wherein the impedance of at least one of the electrodes varies along its respective active region.

17. The electrode device of claim 1, where at least one electrode comprises a section of insulation over a portion of the active region.

18. The electrode device of claim 17, where the section of insulation comprises a pattern selected from the group consisting of: a longitudinal stripe along the portion of the active region, a helical pattern along the portion of the active region; comprises at least one band along the portion of the active region; and a series or pattern of regular or irregular patches along the portion of the active region.

19. The electrode device of claim 1, where the device body further comprises an ink-pad having ink and located on an exterior surface, where the ink pad marks tissue upon contact therewith.

20. The electrode device of claim 1, where the device body further comprises a marking lumen for spraying an ink on an exterior surface of the tissue.

* * * * *